United States Patent
Eidenschink et al.

(10) Patent No.: US 8,012,192 B2
(45) Date of Patent: *Sep. 6, 2011

(54) MULTI-STENT DELIVERY SYSTEM

(75) Inventors: Tracee Eidenschink, Wayzata, MN (US); Jan Weber, Maple Grove, MN (US); Daniel Gregorich, Mound, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2076 days.

This patent is subject to a terminal disclaimer.

(21) Appl. No.: 10/780,937

(22) Filed: Feb. 18, 2004

(65) Prior Publication Data

US 2005/0182473 A1    Aug. 18, 2005

(51) Int. Cl.
*A61F 2/06* (2006.01)
*A61F 11/00* (2006.01)

(52) U.S. Cl. ...... 623/1.11; 606/108; 606/198; 623/1.15; 623/1.23; 604/96.01

(58) Field of Classification Search .................. 623/1.11, 623/1.12, 1.13, 1.23, 1.35; 606/108, 198, 606/194, 195; 604/96.01, 103.03, 171
See application file for complete search history.

(56) References Cited

U.S. PATENT DOCUMENTS

| | | | |
|---|---|---|---|
| 4,448,195 A | 5/1984 | Leveen et al. | 128/344 |
| 4,484,585 A | 11/1984 | Baier | 128/748 |
| 4,601,701 A | 7/1986 | Mueller, Jr. | 604/83 |
| 4,769,005 A | 9/1988 | Ginsburg et al. | 604/53 |
| 4,776,337 A | 10/1988 | Palmaz | 128/343 |
| 4,913,141 A | 4/1990 | Hillstead | 606/108 |
| 4,994,071 A | 2/1991 | MacGregor | 606/194 |
| 4,998,923 A | 3/1991 | Samson et al. | 606/194 |
| 5,019,085 A | 5/1991 | Hillstead | 606/108 |
| 5,122,154 A | 6/1992 | Rhodes | 606/198 |
| 5,195,984 A | 3/1993 | Schatz | 606/195 |
| 5,219,355 A | 6/1993 | Parodi et al. | 606/191 |
| 5,246,421 A | 9/1993 | Saab | |
| 5,257,974 A | 11/1993 | Cox | |
| 5,316,023 A | 5/1994 | Palmaz et al. | 128/898 |
| 5,380,299 A | 1/1995 | Fearnot et al. | |
| 5,397,305 A | 3/1995 | Kawula et al. | 604/96 |
| 5,449,343 A | 9/1995 | Samson et al. | |
| 5,449,382 A | 9/1995 | Dayton | |

(Continued)

FOREIGN PATENT DOCUMENTS

CA    2517380    9/2004

(Continued)

OTHER PUBLICATIONS

Foley et al., "Bifurcation Lesion Stenting", *The Thoraxcentre Journal*, vol. 8, No. 4, (1996).

(Continued)

*Primary Examiner* — Vy Q Bui

(74) *Attorney, Agent, or Firm* — Seager, Tufte & Wickhem LLC

(57) ABSTRACT

A catheter assembly comprises a catheter having a catheter shaft with a first rotatable sheath rotatably disposed thereabout. A first guidewire housing which defines a first guidewire lumen for passage of a first guidewire therethrough is engaged to the first rotatable sheath. A first stent, which when in the reduced stent state, is disposed about at least a portion of the first rotatable sheath. A second stent, which when in the reduced stent state, is positioned adjacent to the first stent.

33 Claims, 17 Drawing Sheets

U.S. PATENT DOCUMENTS

| | | | |
|---|---|---|---|
| 5,477,856 A | 12/1995 | Lundquist | |
| 5,571,086 A | 11/1996 | Kaplan et al. | 604/96 |
| 5,609,627 A | 3/1997 | Goicoechea et al. | 623/1 |
| 5,632,763 A | 5/1997 | Glastra | |
| 5,643,278 A | 7/1997 | Wijay | |
| 5,670,161 A | 9/1997 | Healy et al. | |
| 5,683,345 A | 11/1997 | Waksman et al. | |
| 5,697,971 A | 12/1997 | Fischell et al. | |
| 5,725,519 A | 3/1998 | Penner et al. | |
| 5,744,515 A | 4/1998 | Clapper | |
| 5,749,825 A | 5/1998 | Fischell et al. | |
| 5,755,734 A | 5/1998 | Richter et al. | |
| 5,755,735 A | 5/1998 | Richter et al. | |
| 5,755,778 A | 5/1998 | Kleshinski | |
| 5,772,669 A | 6/1998 | Vrba | |
| 5,776,141 A | 7/1998 | Klein et al. | |
| 5,797,952 A | 8/1998 | Klein | |
| 5,817,100 A | 10/1998 | Igaki | |
| 5,820,595 A | 10/1998 | Parodi | |
| 5,824,055 A | 10/1998 | Spiridigliozzi et al. | 623/1 |
| 5,836,952 A | 11/1998 | Davis et al. | |
| 5,843,027 A | 12/1998 | Stone et al. | |
| 5,873,906 A | 2/1999 | Lau et al. | |
| 5,876,374 A | 3/1999 | Alba et al. | |
| 5,893,868 A | 4/1999 | Hanson et al. | |
| 5,906,640 A | 5/1999 | Penn et al. | |
| 5,908,405 A | 6/1999 | Imran et al. | |
| 5,921,995 A | 7/1999 | Kleshinski | |
| 5,935,161 A | 8/1999 | Robinson et al. | |
| 5,941,908 A | 8/1999 | Goldsteen et al. | |
| 5,951,569 A | 9/1999 | Tuckey et al. | |
| 5,957,929 A | 9/1999 | Brenneman | |
| 5,961,546 A | 10/1999 | Robinson et al. | |
| 5,961,548 A | 10/1999 | Shmulewitz | |
| 6,013,092 A | 1/2000 | Dehdashtian et al. | |
| 6,015,424 A | 1/2000 | Rosenbluth et al. | |
| 6,017,362 A | 1/2000 | Lau | 623/1 |
| 6,027,460 A | 2/2000 | Shturman | 600/585 |
| 6,033,434 A | 3/2000 | Borghi | 623/1 |
| 6,048,350 A | 4/2000 | Vrba | |
| 6,048,361 A | 4/2000 | Von Oepen | 623/1 |
| 6,056,722 A | 5/2000 | Jayaraman | 604/102 |
| 6,056,775 A | 5/2000 | Borghi et al. | 623/1.16 |
| 6,059,813 A | 5/2000 | Vrba et al. | 606/198 |
| 6,071,286 A | 6/2000 | Mawad | 606/108 |
| 6,077,297 A | 6/2000 | Robinson et al. | 623/1.11 |
| 6,090,127 A | 7/2000 | Globerman | 606/194 |
| 6,096,073 A | 8/2000 | Webster et al. | 623/1.16 |
| 6,099,497 A | 8/2000 | Adams et al. | 604/96.01 |
| 6,110,191 A | 8/2000 | Dehdashtian et al. | 606/192 |
| 6,117,156 A | 9/2000 | Richter et al. | 606/194 |
| 6,120,522 A | 9/2000 | Vrba et al. | 606/190 |
| 6,132,450 A | 10/2000 | Hanson et al. | 606/198 |
| 6,143,014 A | 11/2000 | Dehdashtian et al. | 606/192 |
| 6,143,016 A * | 11/2000 | Bleam et al. | 606/198 |
| 6,146,415 A | 11/2000 | Fitz | 623/1.11 |
| 6,152,944 A | 11/2000 | Holman et al. | 623/1.11 |
| 6,165,195 A | 12/2000 | Wilson et al. | 606/194 |
| 6,165,196 A | 12/2000 | Stack et al. | |
| 6,165,210 A | 12/2000 | Lau et al. | 623/1.12 |
| 6,187,015 B1 | 2/2001 | Brenneman | 606/108 |
| 6,190,360 B1 | 2/2001 | Iancea et al. | 604/164.09 |
| 6,190,393 B1 | 2/2001 | Bevier et al. | 606/108 |
| 6,210,380 B1 | 4/2001 | Mauch | 604/284 |
| 6,210,431 B1 | 4/2001 | Power | 623/1.11 |
| 6,221,090 B1 | 4/2001 | Wilson | 606/194 |
| 6,221,097 B1 | 4/2001 | Wang et al. | 623/1.11 |
| 6,224,587 B1 | 5/2001 | Gibson | 604/528 |
| 6,238,410 B1 | 5/2001 | Vrba et al. | 606/198 |
| 6,246,914 B1 | 6/2001 | De la Rama et al. | 607/122 |
| 6,254,593 B1 | 7/2001 | Wilson | 606/1.11 |
| 6,258,052 B1 | 7/2001 | Milo | 604/22 |
| 6,258,073 B1 | 7/2001 | Mauch | 604/284 |
| 6,264,688 B1 | 7/2001 | Herklotz et al. | 623/1.16 |
| 6,280,466 B1 | 8/2001 | Kugler et al. | 623/1.12 |
| 6,287,277 B1 | 9/2001 | Yan | 604/96.01 |
| 6,287,330 B1 | 9/2001 | Johansson et al. | 623/1.13 |
| 6,290,673 B1 | 9/2001 | Shanley | 604/102.02 |
| 6,296,863 B1 * | 10/2001 | Trogolo et al. | 424/404 |
| 6,299,636 B1 | 10/2001 | Schmitt et al. | 623/1.2 |
| 6,302,906 B1 | 10/2001 | Goicoechea et al. | 623/1.11 |
| 6,319,275 B1 | 11/2001 | Lashinski et al. | 623/1.11 |
| 6,322,548 B1 | 11/2001 | Payne et al. | 604/500 |
| 6,350,278 B1 | 2/2002 | Lenker et al. | |
| 6,361,544 B1 | 3/2002 | Wilson et al. | 606/194 |
| 6,361,555 B1 | 3/2002 | Wilson | 623/1.11 |
| 6,364,893 B1 | 4/2002 | Sahatjian et al. | 606/194 |
| 6,371,978 B1 | 4/2002 | Wilson | 623/1.11 |
| 6,375,660 B1 | 4/2002 | Fischell et al. | 606/108 |
| 6,379,372 B1 | 4/2002 | Dehdashtian et al. | 606/192 |
| 6,387,120 B2 | 5/2002 | Wilson et al. | 623/1.11 |
| 6,391,050 B1 | 5/2002 | Broome | 623/1.11 |
| 6,391,052 B2 * | 5/2002 | Buirge et al. | 623/1.47 |
| 6,406,487 B2 | 6/2002 | Brenneman | 623/1.11 |
| 6,406,489 B1 | 6/2002 | Richter et al. | 623/1.16 |
| 6,416,529 B1 | 7/2002 | Holman et al. | 606/194 |
| 6,436,104 B2 | 8/2002 | Hojeibane | 606/108 |
| 6,443,980 B1 | 9/2002 | Wang et al. | 623/1.35 |
| 6,471,672 B1 | 10/2002 | Brown et al. | |
| 6,475,166 B1 | 11/2002 | Escano | 600/585 |
| 6,482,211 B1 | 11/2002 | Choi | 606/108 |
| 6,488,694 B1 | 12/2002 | Lau et al. | 606/194 |
| 6,508,835 B1 | 1/2003 | Shaolian et al. | 623/1.35 |
| 6,514,281 B1 | 2/2003 | Blaeser et al. | 623/1.12 |
| 6,520,983 B1 | 2/2003 | Colgan et al. | 623/1.11 |
| 6,520,988 B1 | 2/2003 | Colombo et al. | 623/1.35 |
| 6,530,947 B1 | 3/2003 | Euteneuer et al. | 623/1.11 |
| 6,533,805 B1 | 3/2003 | Jervis | 623/1.11 |
| 6,540,719 B2 | 4/2003 | Bigus et al. | 604/96.01 |
| 6,554,841 B1 | 4/2003 | Yang | 606/108 |
| 6,569,180 B1 | 5/2003 | Sirhan et al. | |
| 6,582,459 B1 | 6/2003 | Lau et al. | 623/1.11 |
| 6,589,262 B1 | 7/2003 | Honebrink et al. | 606/191 |
| 6,596,020 B2 | 7/2003 | Vardi et al. | 623/1.11 |
| 6,599,315 B2 | 7/2003 | Wilson | 623/1.11 |
| 6,602,226 B1 | 8/2003 | Smith et al. | 604/103.05 |
| 6,607,506 B2 | 8/2003 | Kletschka | 604/96.01 |
| 6,613,067 B1 | 9/2003 | Johnson | 606/194 |
| 6,629,981 B2 | 10/2003 | Bui et al. | 606/108 |
| 6,629,992 B2 | 10/2003 | Bigus et al. | |
| 6,660,030 B2 | 12/2003 | Shaolian et al. | 623/1.11 |
| 6,669,718 B2 | 12/2003 | Basselink | 623/1.11 |
| 6,692,483 B2 * | 2/2004 | Vardi et al. | 604/529 |
| 6,997,946 B2 * | 2/2006 | Girton et al. | 623/1.15 |
| 7,070,613 B2 | 7/2006 | Weber et al. | |
| 7,422,579 B2 | 9/2008 | Wahr et al. | |
| 2001/0049548 A1 | 12/2001 | Vardi et al. | 623/1.11 |
| 2002/0019664 A1 | 2/2002 | Douglas | 623/1.35 |
| 2002/0019665 A1 | 2/2002 | Dehdashtian et al. | 623/1.35 |
| 2002/0022874 A1 | 2/2002 | Wilson | 623/1.11 |
| 2002/0038140 A1 | 3/2002 | Yang et al. | 623/1.12 |
| 2002/0038141 A1 | 3/2002 | Yang et al. | 623/1.12 |
| 2002/0072755 A1 | 6/2002 | Bigus et al. | 606/108 |
| 2002/0111675 A1 | 8/2002 | Wilson | 623/1.35 |
| 2002/0116045 A1 | 8/2002 | Eidenschink | 623/1.11 |
| 2002/0120320 A1 | 8/2002 | Wang et al. | 623/1.11 |
| 2003/0023298 A1 | 1/2003 | Jervis | 623/1.11 |
| 2003/0028211 A1 | 2/2003 | Crocker et al. | 606/192 |
| 2003/0055483 A1 | 3/2003 | Gumm | 623/1.11 |
| 2003/0055484 A1 | 3/2003 | Lau et al. | 623/1.13 |
| 2003/0114912 A1 | 6/2003 | Sequin et al. | 623/1.11 |
| 2003/0130716 A1 | 7/2003 | Weber et al. | 623/1.11 |
| 2003/0181923 A1 | 9/2003 | Vardi | 606/108 |
| 2003/0195546 A1 | 10/2003 | Solar et al. | 606/192 |
| 2005/0027248 A1 * | 2/2005 | Suzuki et al. | 604/103 |
| 2008/0119923 A1 | 5/2008 | Tran et al. | |

FOREIGN PATENT DOCUMENTS

| | | |
|---|---|---|
| CA | 2533306 | 4/2005 |
| CA | 2556693 | 9/2005 |
| CA | 2569657 | 12/2005 |
| DE | 297 01 758 | 5/1997 |
| EP | 1601312 | 9/2007 |
| FR | 2 678 508 A1 | 1/1993 |
| WO | 0044307 | 8/2000 |
| WO | 03/017872 A1 | 3/2003 |
| WO | 03/055414 | 7/2003 |

| | | |
|---|---|---|
| WO | 03/061529 | 7/2003 |
| WO | 2004/075792 | 9/2004 |
| WO | 2005/025458 | 3/2005 |
| WO | 2005067818 | 7/2005 |
| WO | 2005070334 | 8/2005 |
| WO | 2005709902 | 9/2005 |
| WO | 2005122958 | 12/2005 |

OTHER PUBLICATIONS

Schampaert, MD, Erick et al., "The V-Stent: A Novel Technique for Coronary Bifurcation Stenting", *Catheterization and Cardiovascular Diagnosis*, 39:320-326 (1996).

Pomerantz, MD, et al., "Distortion of Palmaz-Schatz Stent Geometry Following Side-Branch Balloon Dilation Through the Stent in a Rabbit Model", *Catheterization and Cardiovascular Diagnosis*, 40:422-426 (1997).

Palmaz, MD, et al., "Aortic Bifurcation Stenosis: Treatment with Intravascular Stents", *Journal of Vascular and Interventional Radiology*, vol. 2, No. 3, pp. 319-323 (Aug. 1991).

Oda, MD., et al., "Fork Stenting for Bifurcational Lesion", Journal of Interventional Cardiology, vol. 9, No. 6, pp. 445-454 (Dec. 1996).

Nakamura et al., "Techniques for Palmaz-Schatz Stent Deployment in Lesions With a Large Side Branch", Catheterization and Cardiovascular Diagnosis, vol. 34, pp. 353-361 (1995).

U.S. Appl. No. 10/375,689, filed Feb. 27, 2003, Eidenschink.
U.S. Appl. No. 10/747,546, filed Dec. 29, 2003, Eidenschink et al.
U.S. Appl. No. 10/657,472, filed Sep. 8, 2003, Eidenschink, et al.
U.S. Appl. No. 10/757,646, filed Jan. 13, 2004, Eidenschink, et al.
U.S. Appl. No. 10/784,337, filed Feb. 23, 2004, Eidenschink, et al.
U.S. Appl. No. 10/863,724, filed Jun. 8, 2004, Eidenschink, et al.

"Medical Urethanes Overview," Noveon, the Specialty Chemicals Innovator, 11 pages, prior to Jan. 13, 2004.

\* cited by examiner

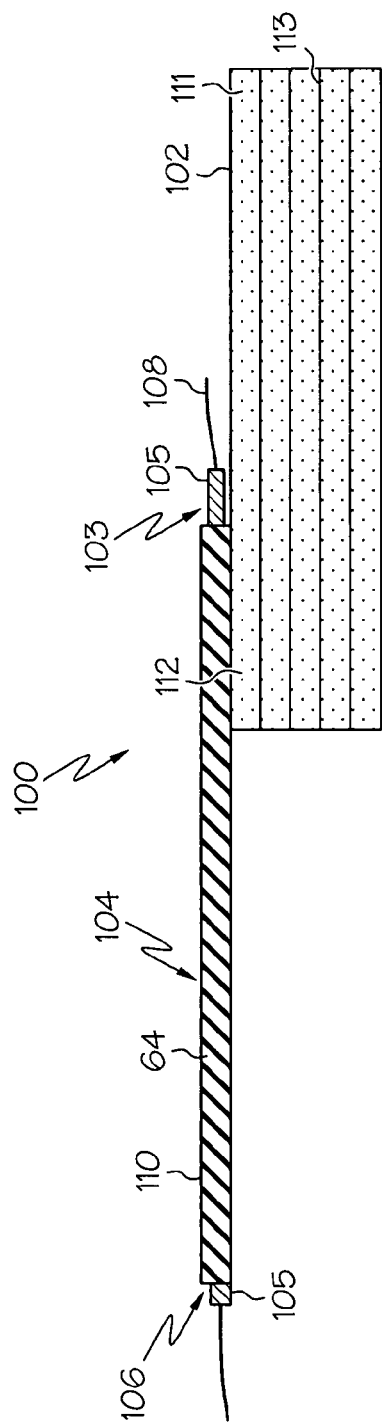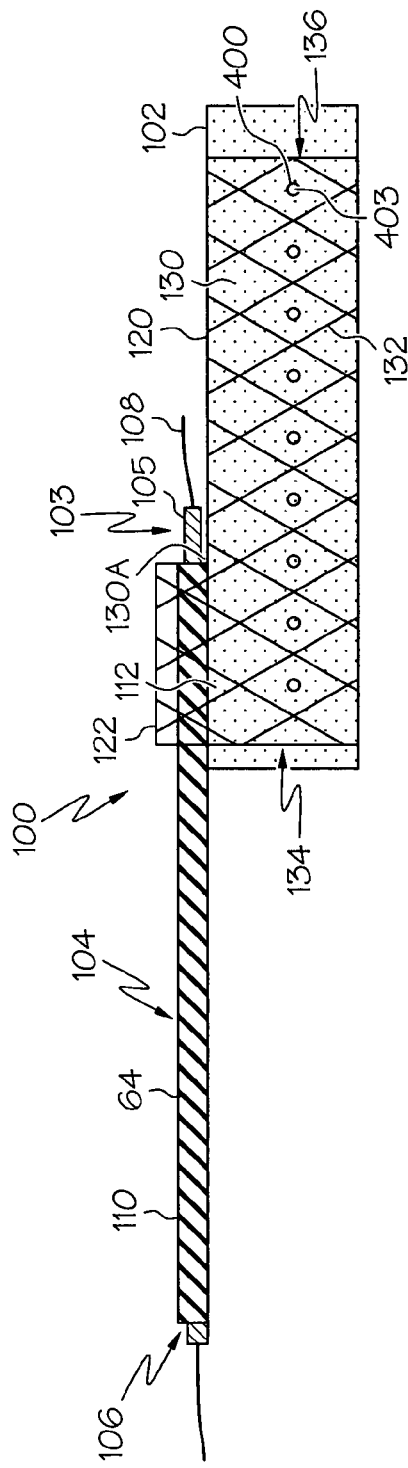

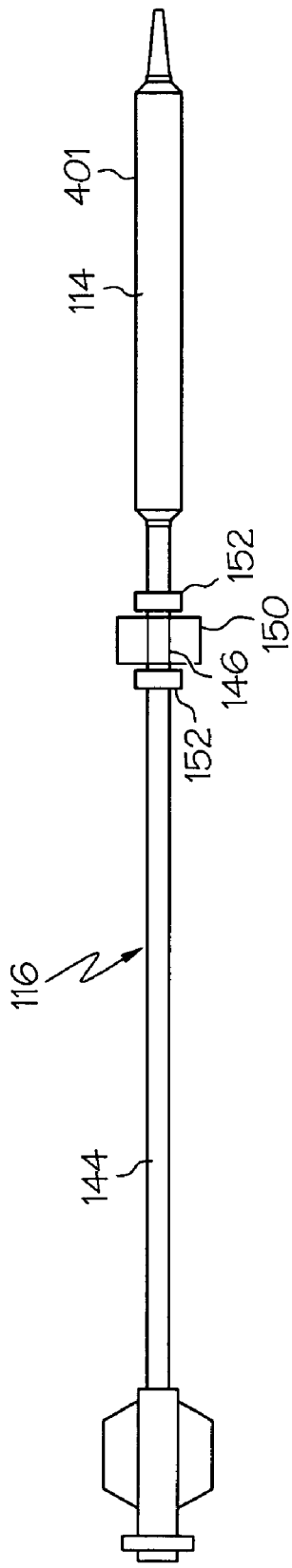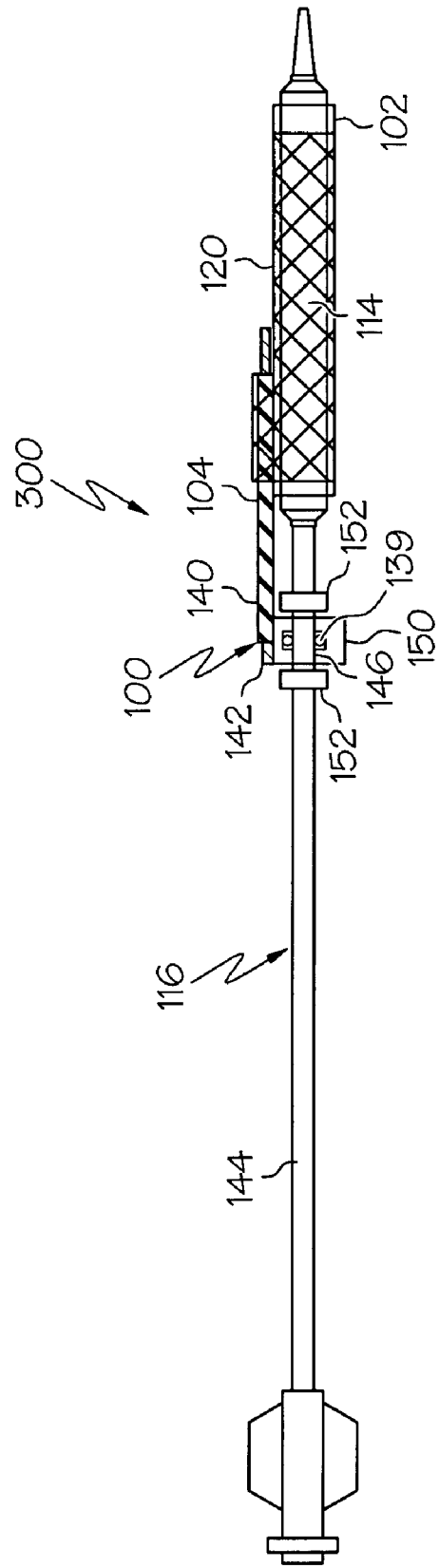

MULTI-STENT DELIVERY SYSTEM

CROSS-REFERENCE TO RELATED APPLICATIONS

Not Applicable

STATEMENT REGARDING FEDERALLY SPONSORED RESEARCH

Not Applicable

BACKGROUND OF THE INVENTION

Description of the Related Art

Catheter systems such as angioplasty catheters, and stent delivery systems, as well as the stents associated therewith, are widely used in the treatment of stenoses, aneurysms, lesions, and other abnormalities within blood vessels and other body lumens. Intravascular stents are used in coronary, renal, and carotid arteries, for example, to maintain an open passage through the artery. In patients whose coronary heart disease consists of focal lesions, stents have proven effective. For example, where only a single coronary artery is clogged or where there are short blockages in more than a single artery, stents have been used with a great amount of success. An intravascular stent may be positioned in a clogged artery by a catheter and is often set in place by inflating a balloon upon which the stent is mounted. This expands the diameter of the stent and opens the previously clogged artery. The balloon is then deflated and removed from the patient while the stent retains an open passage through the artery.

Treatment at bifurcation sites has been difficult. Although efforts have been made to use a stent at bifurcations, these sites have previously been problematic to treat. The specialty stents designed for bifurcations generally need specific alignment, radially as well as longitudinally. For example, U.S. Pat. No. 5,749,825 is representative of a catheter system that is intended to treat stenoses at an arterial bifurcation. The disclosure of U.S. Pat. No. 5,749,825 is hereby incorporated by reference.

Often stent delivery systems are employed to deliver multiple stents to the primary and/or secondary vessels surrounding a vessel bifurcation. One or more catheters may be required to deploy each stent. Stents deployed by such systems generally have an opening or branch which allows for unimpeded blood flow into a side branch artery, and through which one or more branch stents may be subsequently delivered. However, problems are still encountered in orienting such stents relative to the branch openings at the bifurcation of the primary and secondary passages. Moreover, such bifurcated assemblies are typically specially manufactured at an increased cost over a more standard stent intended for single vessel deployment.

In delivering one or more stents to a vessel bifurcation, many current devices rely on the application of torque to the catheter shaft from outside of the patient to properly orient one or more medical devices in the passage. Devices which require torque to be transmitted through the entire length of the catheter in order to orient a stent positioned at a distal end region of the catheter have not been shown to be effective in properly placing and positioning the stent.

Thus, a need exists to provide a catheter which is capable of allowing multiple medical devices, such as stents, to be easily maneuvered, aligned and delivered to the area of a vessel bifurcation or other location(s).

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

Some embodiments of the present invention are directed to a catheter system for delivery of multiple stents or stent segments, wherein at least one of the stents is mounted on the catheter with a freely rotating deployment sheath and assembly such as is described in U.S. patent application Ser. No. 10/375,689, filed Feb. 27, 2003 and U.S. patent application Ser. No. 10/657,472, filed Sep. 8, 2003 both of which are entitled Rotating Balloon Expandable Sheath Bifurcation Delivery; U.S. patent application Ser. No. 10/747,546, filed Dec. 29, 2003 and entitled Rotating Balloon Expandable Sheath Bifurcation Delivery System; and U.S. patent application Ser. No. 10/757,646, filed Jan. 13, 2004 and entitled Bifurcated Stent Delivery System, the entire content of each being incorporated herein by reference.

As used herein the term 'stent' refers to an expandable prosthesis for implantation into a body lumen or vessel and includes devices such as stents, grafts, stent-grafts, vena cava filters, etc. In some embodiments a stent may be at least partially constructed of any of a variety of materials such as stainless steel, nickel, titanium, nitinol, platinum, gold, chrome, cobalt, as well as any other metals and their combinations or alloys. In some embodiments a stent may be at least partially constructed of a polymer material. In some embodiments a stent may be at least partially constructed of a shape-memory polymer or material. In some embodiments a stent may be balloon expandable, self-expandable, hybrid expandable or a combination thereof. In some embodiments a stent may include one or more areas, bands, coatings, members etc that is (are) detectable by imaging modalities such as X-Ray, MRI or ultrasound. In at least one embodiment at least a portion of the stent is at least partially radiopaque. In some embodiments a stent may include one or more therapeutic and/or lubricious coatings applied thereto.

In at least one embodiment at least one stent is disposed about the rotatable sheath.

In at least one embodiment at least two stents are disposed about the rotatable sheath.

In at least one embodiment a catheter system comprises a rotating sheath. A first stent segment is mounted on the sheath. At least one second stent segments is disposed about the catheter adjacent to the rotating sheath.

In at least one embodiments a catheter system employs a first catheter assembly having one or more rotatable sheathes with one or more first stents or stent segments positioned thereon for delivery and one or more second catheter assemblies, which may include one or more second stent segments that may be delivered after the first stent segment(s) are delivered.

In at least one embodiment a catheter system is configured to deploy multiple stent segments wherein one or more stent segments are individually disposed about a separate rotatable sheath prior to delivery. In some embodiments each rotatable sheath is positioned longitudinally adjacent one another and in some embodiments the sheaths may at least partially overlap.

In at least one embodiment a first sheath is rotatably disposed about the catheter and a first stent segment is disposed about the first sheath. A second sheath is rotatably disposed about at least a portion of the first stent and first sheath and may be independently rotatable thereabout.

In at least one embodiment a catheter is configured to deliver at least three stent segments. Prior to delivery, at least one of the at least three stent segments is positioned on a sheath that is rotatable about the catheter. In some embodiments at least two of the stent segments are disposed about one or more rotatable sheaths prior to delivery.

In some embodiments the medical device comprises a secondary guidewire lumen housing, which itself comprises a reinforcing member, such as a polymer tube of PEBAX, peek, polyimide, etc., a braided tube of metal wire or other material, a hypotube, or other device engaged to the sheath and engaged to the collar. In some embodiments an inner member is positioned within the reinforcing member to define the secondary guidewire lumen. In some embodiments the material of the inner member is more flexible than the material of the reinforcing member. In some embodiments the inner member is longer than the reinforcing member and at least one end of the inner member extends beyond at least one end of the reinforcing member.

In at least one embodiment the inner member is concentrically disposed within the reinforcing member. In some embodiments the inner member is asymmetrically disposed within the reinforcing member.

In at least one embodiment the proximal end of the reinforcing member is proximally adjacent to the stent. In some embodiments the proximal end of the reinforcing member is tapered. In at least one embodiment the reinforcing member is positioned such that at least a portion of the reinforcing member is radially offset from the distal end of the stent.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

FIG. 1 is a side view of an embodiment of the invention, comprising a rotating sheath assembly.

FIG. 2 is a side view of the embodiment shown in FIG. 1 shown configured for delivery of a stent.

FIG. 3 is a side view of an embodiment of the invention comprising a catheter assembly. The catheter assembly is provided with a rotating collar.

FIG. 4 is a side view of the catheter assembly of FIG. 3 and further comprising the rotating sheath assembly and stent of FIG. 2.

DETAILED DESCRIPTION OF THE INVENTION

Figure 5:
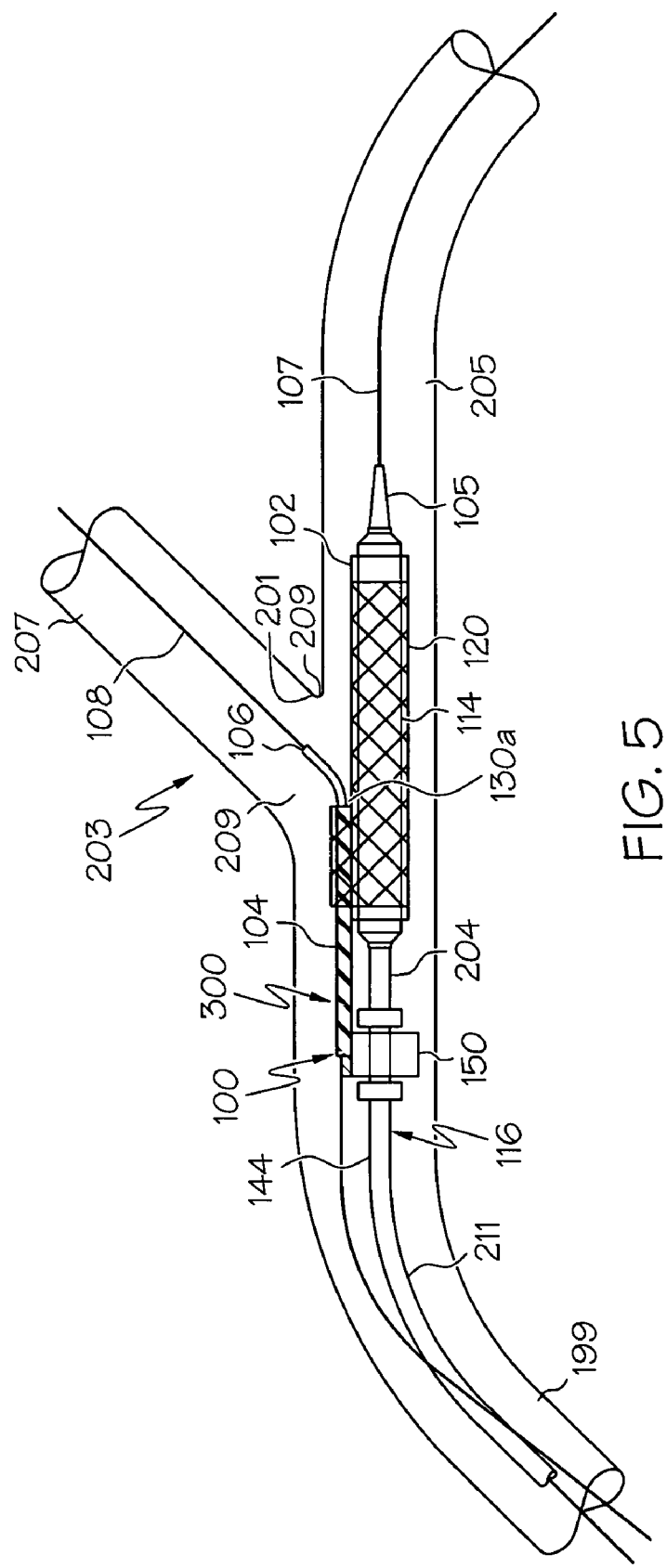
FIG. 5 is a side view of an embodiment of the invention wherein the catheter assembly of FIG. 4 is shown being advanced along a guidewire to a vessel bifurcation prior to delivery of the stent.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Referring now to the drawings which are for the purposes of illustrating embodiments of the invention only and not for purposes of limiting same, in at least one embodiment of the invention, an example of which is shown in FIG. 1 a rotating sheath assembly 100 is shown which comprises a tubular sleeve or sheath 102 and a positioning or secondary guidewire housing 104. The housing 104 defines a secondary guidewire lumen 106 through which a secondary guidewire 108 may be passed.

Though the housing 104 may be constructed of a wide variety of materials including metal plastic, etc., in at least one embodiment the housing 104 is an external reinforcing member or hypotube 64.

The hypotube 64 may comprise stainless steel, one or more polymer materials or other material. In some embodiments the housing 104 is provided with one or more openings 110 along its length. In at least one embodiment the housing 104 is spiral cut to provide at least a continuous opening 110 which acts to provide improve the flexibility of the housing 104.

In at least one embodiment the secondary guidewire housing 104 further comprises an inner shaft 103, about which the hypotube 64 is disposed. Alternatively, the inner shaft 103 and hypotube 64 may be of a single piece construction wherein the housing 104 is formed using a 'bumped' extrusion and then scored for improved flexibility. In at least one embodiment the inner shaft 103 is a flexible hollow tubular member which extends distally beyond the distal end of the hypotube 64. In some embodiments both the hypotube 64 and the inner shaft 103 are scored, cut or otherwise provided with improved flexibility over a more rigid continuous shaft. In some embodiments flexibility of the housing 104 may be improved by manufacturing the housing 104, or a portion thereof, to include segmented rings; a pattern of cuts, indentations, etc; and or a corrugated construction.

This distal and/or proximal tips 105 of the inner shaft 103 provides the housing with a flexible protective sheath about the guidewire 108 as it passes out of the secondary guidewire lumen 106. Such a protective covering may prevent the guidewire 108 from excessively rubbing against the wall 201 of the vessel 199, such as in the manner depicted in FIG. 5; even where the secondary guidewire 108 exits the secondary lumen 106 at a significant angle. The inner shaft 103 may be constructed of any of a variety of flexible materials such as: high density polyurethane (HDPE), PEBAX, nylon, urethane, and/or other materials in a single layer, multi-layer and/or braided configuration.

In some embodiments the shaft 144 of the catheter 116 defines a primary guidewire housing 211 through which a primary guidewire 107 may be advanced. In use guidewires 107 and 108 are passed through a lumen or other body vessel 199 to a bifurcation 203. Primary guidewire 107 is then advanced into a primary branch of passage 205 of the bifurcation 203 while the secondary guidewire 108 is advanced into the adjacent or secondary branch 207 of the bifurcation 203. As the system is advanced along both guidewires 107 and 108, as a result of the divergent paths defined by the guidewires 107 and 108, the rotatable sleeve 104 will rotate the stent 120 into a desired position so that the secondary opening 130a of the stent is aligned with the secondary passage 207. In at least one embodiment, the system 300 is a fixed wire system, and as such the use of the primary guidewire is unnecessary. In some embodiments the catheter 116 is an over-the-wire, MONORAIL®, or other type of catheter 116 which requires the primary guidewire 107.

In some embodiments at least a distal portion of the housing 104 is engaged to at least a proximal portion of the sheath 102 at an engagement site 112. The manner or mechanism of engagement between the sheath and housing 104 may be by bonding, welding, adhering adhesively engaging, mechanically engaging or otherwise connecting the surfaces of the respective sheath 102 and housing 104.

The sheath 102 is a hollow tube of sheath material that is configured to be placed over the balloon 114 or other region of a catheter 116, such as in the manner illustrated in FIGS. 3 and 4. The sheath 102 is further configured to be rotatable about the catheter shaft and/or balloon 114, even when a stent 120 has been positioned about and/or affixed to the sheath 102.

In order to ensure that the sheath 102 is rotatable about a balloon 114, even with a stent 120 crimped on to the sheath 102 and the catheter is being advanced through the a body, the sheath 102 may be constructed of a variety of low friction materials such as PTFE, HDPE, etc. In at least one embodiment the sheath 102 is at least partially constructed of a hydrophilic material, such as hydrophilic polymers such as; TECOPHILIC® material available from Thermedics Polymer Products, a division of VIASYS Healthcare of Wilmington, Mass.; TECOTHANE®, also available from Thermedics Polymer Products; hydrophilic polyurethanes, and/or aliphatic, polyether-based thermoplastic hydrophilic polyurethane; and any other material that provides the sheath 102 with the ability to rotate freely about the balloon 114 when in the "wet" state, such as when the catheter is exposed to body fluids during advancement through a vessel. Suitable sheath materials may also provide the sheath with rotatability in the "dry", or pre-insertion, state, but with the application of a greater amount of force than when in the wet state, such materials are referred to herein as being tecophilic.

A sheath 102 at least partially constructed from tecophilic material provides the sheath 102 with the ability to rotate freely about the balloon 114 when in the "wet" state, such as when the catheter is exposed to body fluids during advancement through a vessel. The tecophilic sheath 102 is also capable of rotation in the "dry", or pre-insertion, state, but with the application of a greater amount of force than when in the wet state.

In some embodiments the sheath 102 may be constructed of one or multiple materials, in one or more layers. For example, the sheath 102 may comprise an outer layer of a softer material than that of the material used in constructing an inner layer, such as has been previously described. In some embodiments, an example of which is shown in FIG. 1, the sheath 102 may be comprised of a matrix of a first material 111 and have one or more supportive stripes, strands, members or areas of a second supportive material 113 within, external to or internal to such a matrix.

The composition of the sheath 102 material, whether a single, multiple layer or stripe reinforced extrusion may include essentially any appropriate polymer or other suitable materials. Some example of suitable polymers include Hydrophilic Polyurethanes, Aromatic Polyurethanes, Polycarbonate base Aliphatic Polyurethanes, Engineering polyurethane, Elastomeric polyamides, block polyamide/ethers, polyether block amide (PEBA, for example available under the trade name PEBAX), and Silicones, Polyether-ester (for example a polyether-ester elastomer such as Arnitel available from DSM Engineering Plastics), Polyester (for example a polyester elastomer such as Hytrel available from Du Pont), or linear low density polyethylene (for example Rexell).

Example of suitable re-inforcing materials whether alone or blended with other materials, mixtures or combination or copolymers include all Polyamides (for example, Durethan available from Bayer or Cristamid available from ELF Atochem), polyethylene (PE). Marlex high-density polyethylene, polyetheretherketone (PEEK), polyimide (PI), and polyetherimide (PEI), liquid crystal polymers (LCP), and Acetal (Delrin or Celcon).

In some embodiments the inner surface of the sheath 102 or the outer surface of the balloon 114 may include a coating of one or more low friction materials or include one or more low friction materials in its construction. Such a coating 401 is shown in FIG. 3, as being depicted on the surface of the balloon 114 before assembly 100 has been placed thereabout, such as is depicted in FIG. 4. Coating 401 may however by placed between the balloon 114 and sheath 102 at any time. Some examples of a suitable coating material include but are not limited to: hydrogel, silicon, and/or BIOSLIDE® available from SciMed Life Systems, Inc. of Maple Grove Minn.

As mentioned above, the sheath 102 is configured to be freely rotatable about a balloon of a catheter even when a stent 120, such as is shown in FIGS. 2 and 4 is crimped onto the sheath 102. When properly positioned on the sheath 102, a proximal portion 122 of the stent 120 is also disposed about at least a portion of the secondary guidewire housing 104. When properly positioned about the sheath 102 and the housing 104, at least a portion of the housing 104 and/or the secondary guidewire 108 extends distally through a cell opening 130 of the stent 120.

Figure 6:
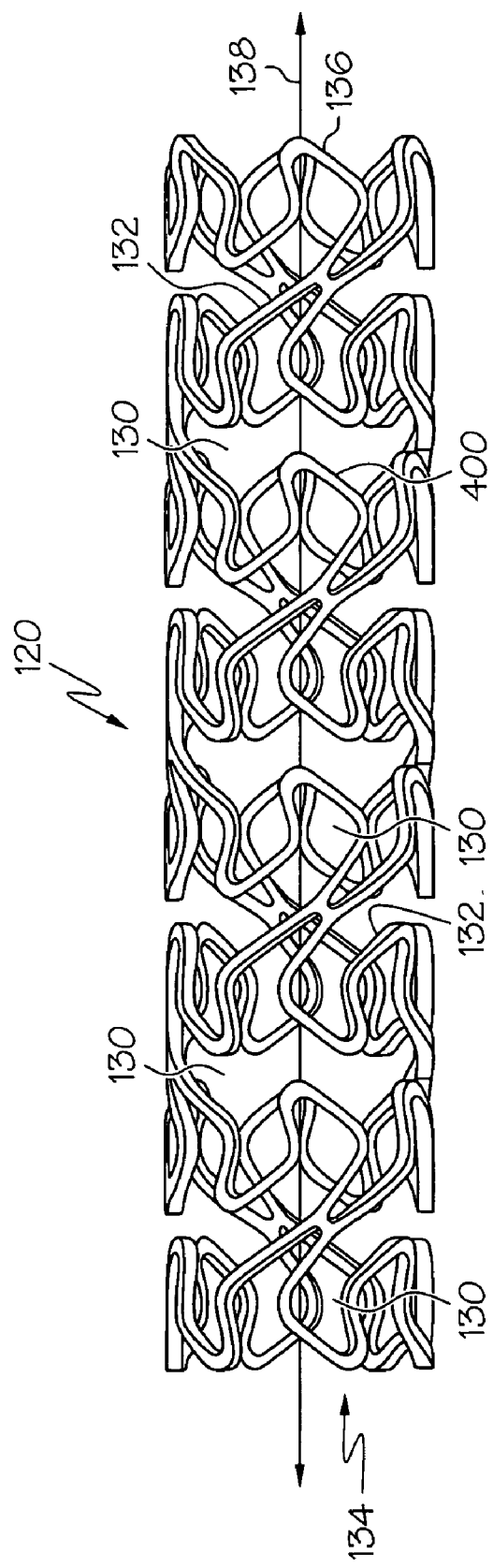
FIG. 6 is a side perspective view of an embodiment of the invention comprising a stent, such as that shown in FIG. 2.

Stent 120 may be a stent, such as is shown in FIG. 6, which is at least partially constructed of a plurality of interconnected struts, connectors or members 132. The stent 132 defines a proximal opening 134, a distal opening 136 and a flow path 138 therebetween. The cell openings 130 are in fluid communication with the flow path 138.

When the secondary guidewire 108 and/or the secondary guidewire housing 104 is threaded through one of the cell openings 130 when the stent is positioned onto the assembly 100, such as is shown in FIGS. 2 and 4, the members 132 that define the selected cell opening 130a, as well as the shape of the opening 130a through which the secondary guidewire 108 exits the stent, may be distorted or modified in order to accommodate the passage of secondary guidewire 108 and/or the secondary guidewire housing 104 therethrough.

Figure 7:
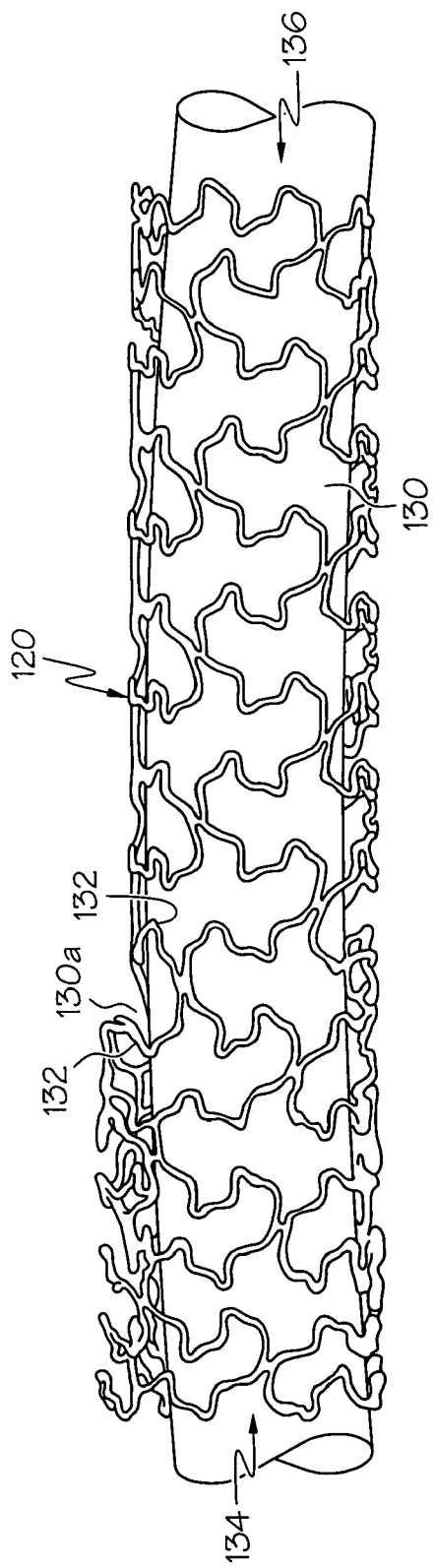
FIG. 7 is a side perspective view of the stent shown in FIG. 6 wherein a side branch opening is shown.
Figure 8:
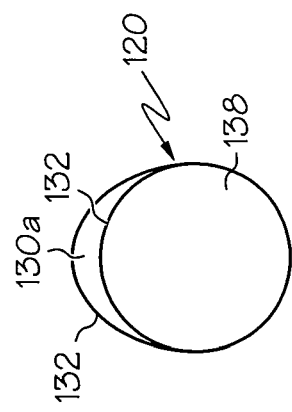
FIG. 8 is a cross-sectional view of the stent of FIG. 7.

The modified cell opening 130a, hereinafter referred to as secondary opening 130a, is positioned on the stent 120 between the proximal opening 134 and the distal opening 136 and is depicted in FIGS. 7 and 8. It is noted that any type of stent may be provided with secondary opening 130a and that the present invention is not limited to only the particular type of stent design, configuration or structure shown.

It should be noted that when the stent 120 is placed on the assembly in the manner described above, the distortion of the secondary opening 130a and the adjacent members 132 is of a minimal extent, and is provide only to allow sliding passage of the secondary guidewire 108, and if desired a distal portion of the secondary guidewire housing 104, through the secondary opening 130a. As such, the actual size of the secondary opening 130a may be substantially similar, or only marginally different than that of the surrounding cell openings 130.

It should also be further noted that while stent 120 may be a standard "single vessel" stent that is provided with a secondary opening 130a in the manner described above, the stent 120 may also be a bifurcated stent having a trunk or stem portion, with one or more leg portions and/or branch openings adjacent thereto, through one of which the secondary guidewire may be passed. Such bifurcated stents and stent assemblies are well known in the art.

Figure 9:
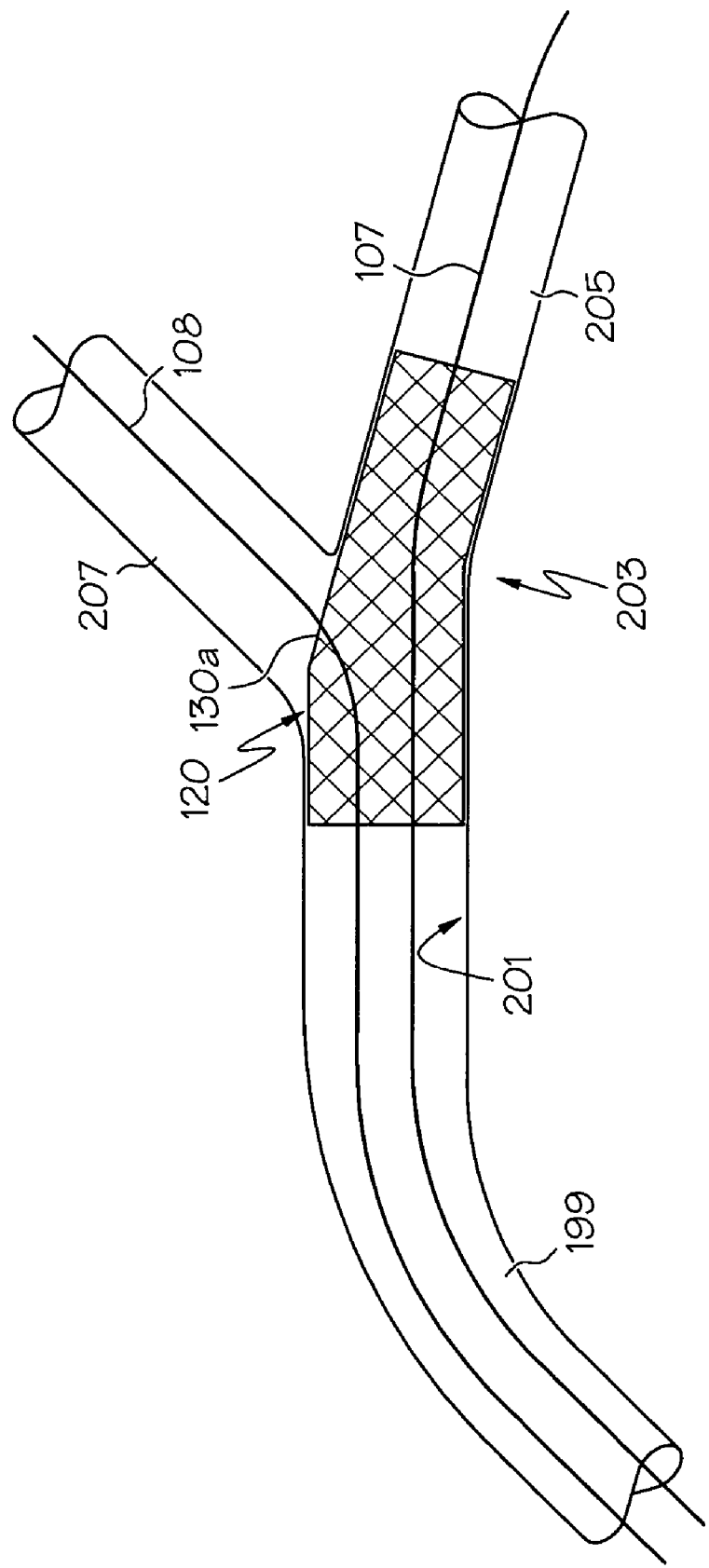
FIG. 9 is a side view of a vessel wherein the stent depicted in FIG. 5, has been delivered from the catheter assembly and the assembly subsequently withdrawn from the vessel(s).

In at least one embodiment the stent 120, or one or more portions thereof, may be configured to deliver one or more therapeutic agents to a delivery site such as within the vessel 199 or one or more areas adjacent thereto, such as shown in FIGS. 5 and 9. In some embodiments one or stent members 132, such as is shown in FIG. 6, maybe configured to include one or more holes, notches, or other surface features to which one or more therapeutic agents 400 may be placed for delivery to the aneurysm site. A therapeutic agent may be placed on the stent in the form of a coating. In at least one embodiment the coating includes at least one therapeutic agent and at least one polymer.

A therapeutic agent may be a drug, a non-genetic agent, a genetic agent, etc. Some examples of suitable non-genetic therapeutic agents include but are not limited to: anti-thrombogenic agents such as heparin, heparin derivatives, urokinase, and PPack (dextrophenylalanine proline arginine chloromethylketone); anti-proliferative agents such as enoxaprin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine and ropivacaine; anti-coagulants such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factor inhibitors, growth factor receptor antagonists, transcriptional activators, and translational promoters, vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin; bifunctional molecules consisting of an antibody and a cytotoxin; cholesterol-lowering agents; vasodilating agents; and agents which interfere with endogenous vascoactive mechanisms, and any combinations thereof.

Where an agent includes a genetic therapeutic agent, such a genetic agent may include but is not limited to: anti-sense DNA and RNA; DNA coding for anti-sense RNA, tRNA or rRNA to replace defective or deficient endogenous molecules; angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor; cell cycle inhibitors including CD inhibitors, thymidine kinase ("TK") and other agents useful for interfering with cell proliferation; at least one of the family of bone morphogenic proteins ("BMP's") such as BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Any of BMP-2, BMP-3, BMP-4, BMP-5, BMP-6 and BMP-7; dimeric proteins such as homodimers, heterodimers, or combinations thereof, alone or together with other molecules; molecules capable of inducing an upstream or downstream effect of a BMP such as "hedgehog" proteins, or the DNA's encoding them and any combinations thereof.

Where a therapeutic includes cellular material, the cellular material may include but is not limited to: cells of human origin (autologous or allogeneic); cells of non-human origin (xenogeneic) and any combination thereof. Some examples of cellular material include but are not limited to the following:

SP—(side population cells) These cells are thought to be some of the most primitive adult stem cells. They are isolated by a specific FACS technique utilizing the ability of SP cells to exclude Hoechst dye from the nucleus. In addition to bone marrow, SP cells have been isolated from most tissues, including: cardiac and skeletal muscle. By the more common surface protein identification these cells are Lin$^-$, Sca-1$^+$, c-Kit$^+$, CD43$^+$, CD45$^+$, CD34$^-$ Lin$^-$—(lineage negative cells) This group of cells is isolated from the bone marrow and all cells which have differentiated to a specific lineage (e.g. red blood cells) have been removed. Therefore leaving all of the stem and progenitor cells. This is beneficial because all primitive cells remain, but may reduce efficiency by including irrelevant, primitive cell types.

Lin$^-$CD34$^+$—Although CD34$^+$ cells have received much attention, many articles have been published lately which suggest the most primitive bone marrow derived stem cells are CD34$^-$ Lin$^-$CD34$^+$—Presence of the cell surface protein CD34 has been used to identify hematopoietic stem cells. However, the marker is also present on progenitor cells and white blood cells of various levels of maturity.

Lin$^-$cKit$^+$—cKit is the cell surface receptor for stem cell factor, and therefore a logical choice for stem cell selection. Most widely studied from bone marrow sources, but have also been isolated from the heart.

MSC—(mesenchymal stem cells) Named so because ordinarily these cells differentiate into cells of mesenchymal tissues (e.g. bone, cartilage, fat), but may also differentiate into cardiomyocytes under certain conditions. Easily isolated from bone marrow and, unlike hematopoietic stem cells, proliferate in vitro. A subpopulation of MSCs has been shown to self-renew faster and have a greater potential for multipotential differentiation than the general MSC population. D. Prockop from Tulane U. is publishing in this area.

Cord Blood Cells—Derived from the blood remaining in the umbilical vein following child birth. This blood has been shown to contain a higher percentage of immature stem cells or progenitor cells. Typically, a matched donor must be found for patients, but a lower incidence of graft versus host disease compared to stem cell isolation from adult blood has been reported. Disadvantages include: insufficient cell number in small blood volumes, unforeseen congenital defects, and contamination by mother's blood which is likely not HLA matched.

Cardiac or other tissue derived stem cells—Most work to date has focused on isolating stem cells from bone marrow. This is due to extensive work in improving bone marrow transplants for chemotherapy and leukemia treatments. However, there is evidence that similar stem cells which can be identified by similar means (e.g. SP, cKit) can be isolated from other tissues (e.g. fat, cardiac muscle).

Whole bone marrow—An "it's in there" approach where whole bone marrow (filtered for bone particles) is transplanted. Benefits include: little processing, all stem and progenitor cells are present, and matrix proteins and growth factors may also be present. Downside—if one or two stem cell types are responsible for cardiac improvement they will only be present in very low numbers.

BM-MNCs—(bone marrow mononuclear cells) Separated from whole bone marrow by a density gradient centrifugation procedure, this population contains non-granular white blood cells, progenitor cells, and stem cells.

EPCs—(endothelial progenitor cells) Isolated from bone marrow based on cell surface markers, these cells will become endothelial cells. In theory, these cells will form new blood vessels when delivered to ischemic tissue.

Skeletal myoblasts—(or satellite cells) These cells are responsible for the regeneration of skeletal muscle following injury. They have the ability to fuse with other myoblasts or damaged muscle fibers. Cardiac muscle therapies assume these cells can integrate into the host tissue and improve tissue properties or functionally participate in contraction.

MDCs—(muscle derived cells) A population of cells isolated from adult skeletal muscle which are similar to myoblasts. The isolation technique preplating entails collecting cells which attach to culture dishes at different times after biopsy. Cells with the best potential plate in the 6$^{th}$ group and takes several days to obtain. Investigators working with these cells claim they are a refined population of myoblasts and should result in higher engraftment efficiencies and efficacious procedures.

Go cells—Recently isolated from adult skeletal muscle, these non-satellite cells express GATA-4 and, under certain in vitro growth conditions, progress to spontaneously beating cardiomyocyte-like cells.

Endothelial cells—Transplantation of autologous endothelial cells along with a fibrin matrix induced angiogenesis and improved cardiac function in an ischemic sheep model.

Adult Cardiomyocytes

Fibroblasts—Easily obtained from adult tissues, fibroblasts may provide growth factors or participate in the would healing response. Fibroblast play a critical role in wound healing; the synthesis and deposition of extracellular matrix. Fibroblasts commonly become contractile in wound healing environments.

Smooth muscle cells—Isolated from arteries, these cells may participate or encourage angiogenesis and/or beneficial cardiac remodeling following MI.

MSCs+5-aza—Culture of mesenchymal stem cells with 5-aza forces differentiation into cardiomyocytes. These cells beat spontaneously after treatment.

Adult cardiac fibroblasts+5-aza—In theory, in vitro treatment of cardiac fibroblasts with 5-aza will result in differentiation into myogenic cells.

Genetically modified cells—Isolation of cells from the patient and genetically modifying them in vitro to encourage production of proteins or differentiation into a cell type which will be beneficial for treating heart failure.

Tissue engineered grafts—Isolation of cells from the patient which are then seeded onto and cultured within resorbable scaffolds (e.g. collagen, PLGA). These cell seeded constructs are then implanted into the patient.

MyoD scar fibroblasts—MyoD family of transcription factors prompt skeletal muscle cell differentiation in fibroblasts. Procedure involves isolation of cardiac scar fibroblasts, genetic transfection with MyoD in vitro and delivery of the cells to the heart to encourage myogenesis.

Pacing cells—Genetically modified fibroblasts which become electrically conducting and signal generators.

Embryonic stem cell clones—Use of cloning technology to produce cardiomyocytes, progenitors, or stem cells which are genetically identical to the patient.

Embryonic stem cells—These cells are the most primitive of cells and will differentiate into functional cardiomyocytes under certain conditions. Both political and technological hurdles must be overcome before commercialization of this technology.

Fetal or neonatal cells—Isolated from the heart of donors, these cells may incorporate into host tissue without immune rejection. Some cardiomyocyte progenitor cells must be present due to the continued growth of the heart in fetal and neonatal humans.

Immunologically masked cells—Allogeneic cell sources (e.g. donor cardiomyocytes) are currently unfeasible due to immune rejection. However, masking technologies have been developed which could make this technology feasible.

Tissue engineered grafts—Isolation of cells from a donor which are then seeded onto and cultured within resorbable scaffolds (e.g. collagen, PLGA). These cell seeded constructs are then implanted into the host or recipient.

Genetically modified cells—Isolation of cells from a donor and genetically modifying them in vitro to encourage production of proteins or differentiation into a cell type which will be beneficial for treating heart failure. The modified cells will then be transplanted into the host or patient.

Teratoma derived cells—A teratocarcinoma is a form of cancer in which the tumor is composed of a heterogeneous mixture of tissues. Through isolation of cells from this tumor and in vitro manipulation and culture a neuronal cell line has been developed. Layton Biosciences has successfully used these cells to form new brain tissue in stroke patients. Similar techniques may be used to produce a myogenic cell line.

Where a therapeutic agent comprises at least one polymer agent or coating, the at least one coating may include but is not limited to: polycarboxylic acids; cellulosic polymers, including cellulose acetate and cellulose nitrate; gelatin; polyvinylpyrrolidone; cross-linked polyvinylpyrrolidone; polyanhydrides including maleic anhydride polymers; polyamides; polyvinyl alcohols; copolymers of vinyl monomers such as EVA; polyvinyl ethers; polyvinyl aromatics; polyethylene oxides; glycosaminoglycans; polysaccharides; polyesters including polyethylene terephthalate; polyacrylamides; polyethers; polyether sulfone; polycarbonate; polyalkylenes including polypropylene, polyethylene and high molecular weight polyethylene; halogenated polyalkylenes including polytetrafluoroethylene; polyurethanes; polyorthoesters; proteins; polypeptides; silicones; siloxane polymers; polylactic acid; polyglycolic acid; polycaprolactone; polyhydroxybutyrate valerate and blends and copolymers thereof; coatings from polymer dispersions such as polyurethane dispersions (BAYHDROL®, etc.), fibrin, collagen and derivatives thereof; polysaccharides such as celluloses, starches, dextrans, alginates and derivatives; hyaluronic acid; squalene emulsions; polyacrylic acid, a copolymer of polylactic acid and polycaprolactone; medical-grade biodegradable materials such as PGA-TMC, Tyrosine-Derived Polycarbonates and arylates; polycaprolactone co butyl acrylate and other co polymers; Poly-L-lactic acid blends with DL-Lactic Acid; Poly(lactic acid-co-glycolic acid); polycaprolactone co PLA; polycaprolactone co butyl acrylate and other copolymers; Tyrosine-Derived Polycarbonates and arylate; poly amino acid; polyphosphazenes; polyiminocarbonates; polydimethyltrimethylcarbonates; biodegradable CA/PO$_4$'s; cyanoacrylate; 50/50 DLPLG; polydioxanone; polypropylene fumarate; polydepsipeptides; macromolecules such as chitosan and Hydroxylpropylmethylcellulose; surface erodible material; maleic anhydride copolymers; zinc-calcium phosphate; amorphous polyanhydrides; sugar; carbohydrate; gelatin; biodegradable polymers; and polymers dissolvable in bodily fluids; and any combinations thereof.

In at least one embodiment an example of a suitable polymer agent or coating comprises block copolymers comprising at least one A block and at least one B block. The A blocks are preferably soft elastomeric blocks, which are based upon one or more polyolefins, or other polymer with a glass transition temperature at or below room temperature. For example, the A blocks can be polyolefinic blocks having alternating quaternary and secondary carbons of the general formulation: —(CRR'—CH$_2$)$_n$—, where R and R' are, independently, linear or branched aliphatic groups such as methyl, ethyl, propyl, isopropyl, butyl, isobutyl and so forth, or represent cyclic aliphatic groups such as cyclohexane, cyclopentane, and the like, either with or without pendant groups. Preferred polyolefinic blocks include polymeric blocks of isobutylene,

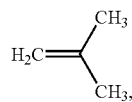

(i.e., polymers where R and R' are methyl groups). Other examples of A blocks include silicone rubber blocks and acrylate rubber blocks.

The B blocks are preferably hard thermoplastic blocks with glass transition temperatures significantly higher than the elastomeric A blocks which, when combined with the soft A blocks, are capable of, inter alia, altering or adjusting the hardness of the resulting copolymer to achieve a desired combination of qualities. Examples of B blocks include polymers of methacrylates or polymers of vinyl aromatics. More specific examples of B blocks include blocks that are (a) formed from monomers of styrene

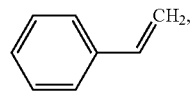

styrene derivatives (e.g., α-methylstyrene, ring-alkylated styrenes or ring-halogenated styrenes or other substituted styrenes where one or more substituents are present on the aromatic ring) or mixtures of the same, collectively referred to herein as "styrenic blocks" or "polystyrenic blocks" or are (b) formed from monomers of methylmethacrylate, ethylmethacrylate, hydroxyethyl methacrylate or mixtures of the same.

The block copolymers are provided in a variety of architectures, including cyclic, linear, and branched architectures. Branched architectures include star-shaped architectures (e.g., architectures in which three or more chains emanate from a single region), comb architectures (e.g., copolymers having a main chain and a plurality of side chains), and dendritic architectures (including arborescent or hyperbranched copolymers).

Some specific examples of such block copolymers include the following: (a) BA (linear diblock), (b) BAB or ABA (linear triblock), (c) B(AB)$_n$, or A(BA)$_n$ (linear alternating block), or (d) X-(AB)$_n$ or X-(BA)$_n$ (includes diblock, triblock and other radial block copolymers), where n is a positive whole number and X is a starting seed, or initiator, molecule. One specific group of polymers have X-(AB)$_n$ structures, which are frequently referred to as diblock copolymers and triblock copolymers where n=1 and n=2, respectively (this terminology disregards the presence of the starting seed molecule, for example, treating A-X-A as a single A block, with the triblock therefore denoted as BAB). A particularly beneficial polymer from this group is polystyrene-polyisobutylene-polystyrene triblock copolymer (SIBS). Where n=3 or more, these structures are commonly referred to as star-shaped block copolymers. Other examples of block polymers include branched block copolymers such as dendritic block copolymers, wherein at least one of the A and B blocks is branched, for instance, where the A blocks are branched and are capped by the B blocks.

Figure 10:
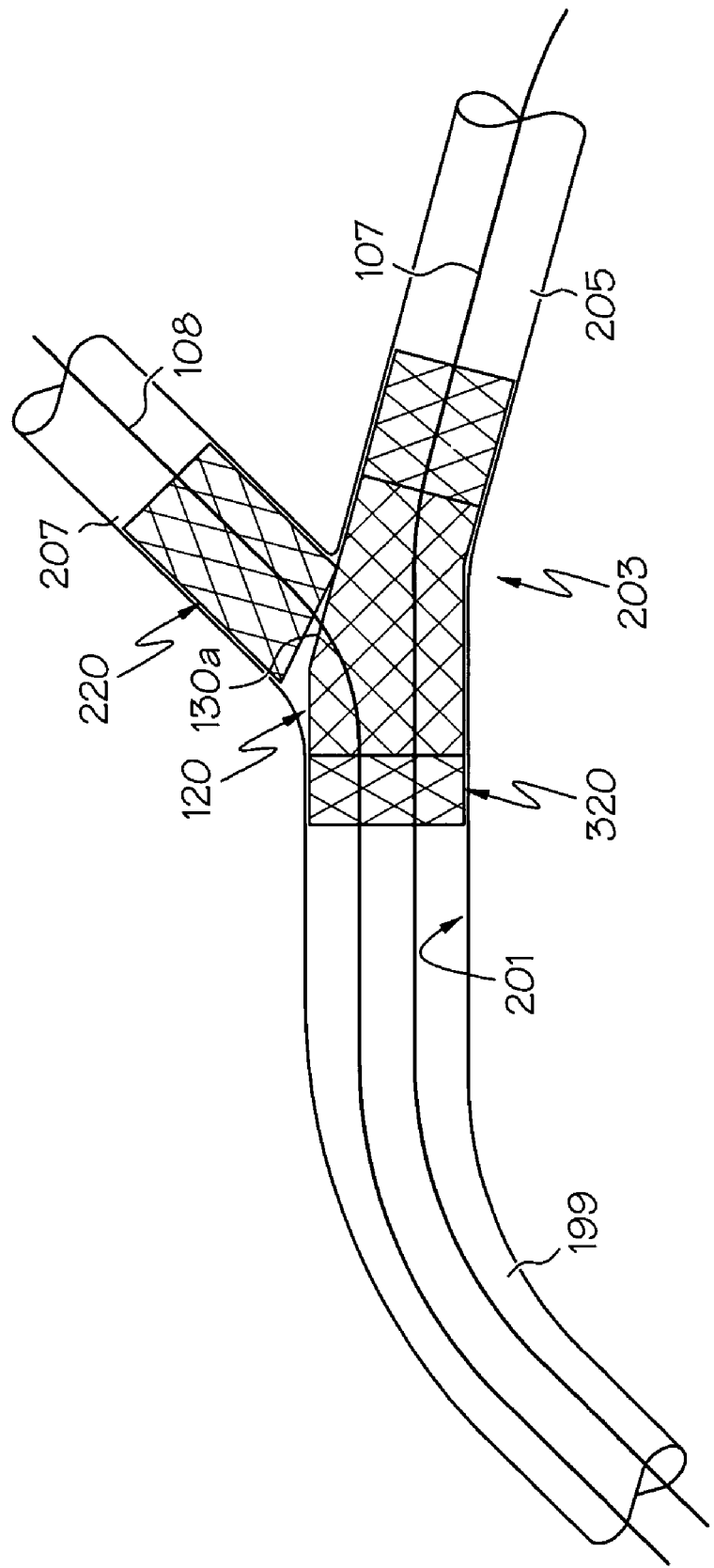
FIG. 10 is a side view of the vessel shown in FIG. 9 wherein multiple stents or stent segments have been delivered by one or more catheter assemblies.

In procedures where stenting or other treatment at a vessel bifurcation 203 is needed a single stent 120, such as is shown in FIG. 9 may be deployed. In some embodiments however one or more additional stents or stent segments 220 and 320 such as are shown in FIG. 10 may be subsequently or simultaneously deployed at or around the bifurcation 203 as well.

A system for deploying such stents may involve a single or multiple catheters, about which one or more of the stents is disposed about one or more rotatable sheaths.

Figure 11:
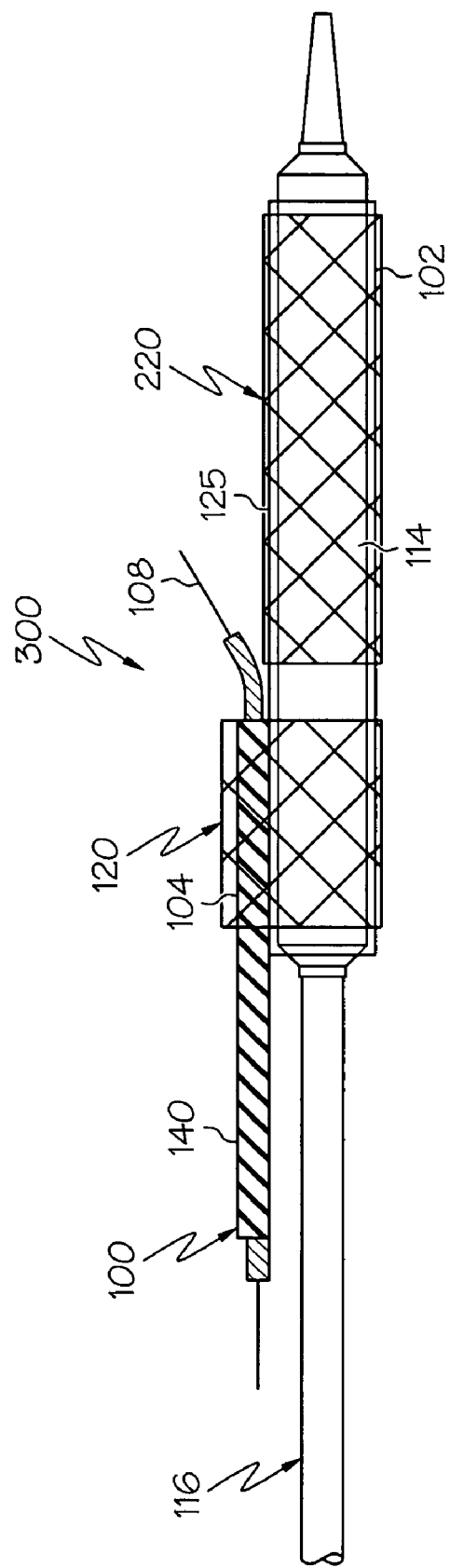
FIG. 11 is cross-sectional side view of an embodiment of the invention wherein a catheter system includes two longitudinally displaced stents disposed about the rotatable sheath.

For example, in at least one embodiment, an example of which is shown in FIG. 11 a catheter 116 is provided with a rotatable assembly 100 which includes the rotatable sheath 102, secondary guidewire housing 104 and a pair of stents 120 and 220.

In some embodiments particularly where one or both stents 120 and 220 are coated with one or more therapeutic agents, as discussed above, the presence of two stents allows a practitioner a high degree of control over dosage of the agent or agents in question by placing desired portions (i.e. 'Y' micrograms and 'Z' micrograms respectively) of the total weight of the agent on the separate stents to provide for the uniform delivery of the entire weight (i.e. 'X' micrograms of the agent, where X=Y+Z).

For example, if an agent having a total weight of 'X' micrograms is desired to be delivered, the first stent 120 may be provided with a 'Y' proportion of the agent and the second stent 220 is provided with the remaining 'Z' portion of the agent. The total weight of the agent may be divided up between the stents in any proportion desired. Furthermore, in some embodiments the total weight of the agent may be proportioned up between more than two stents as well.

As shown both stents 120 and 220 are engaged to the rotatable sheath 102 prior to delivery. In the embodiment shown in FIG. 11, the secondary guidewire housing 104 extends under and through the entire length of the first or proximal stent 120 without exiting through a cell, such as a secondary opening 130a, as shown and described above. However, the distal portion of the secondary guidewire housing 104 and/or the secondary guidewire 108 is radially external to the second or distal stent 220.

Figure 12:
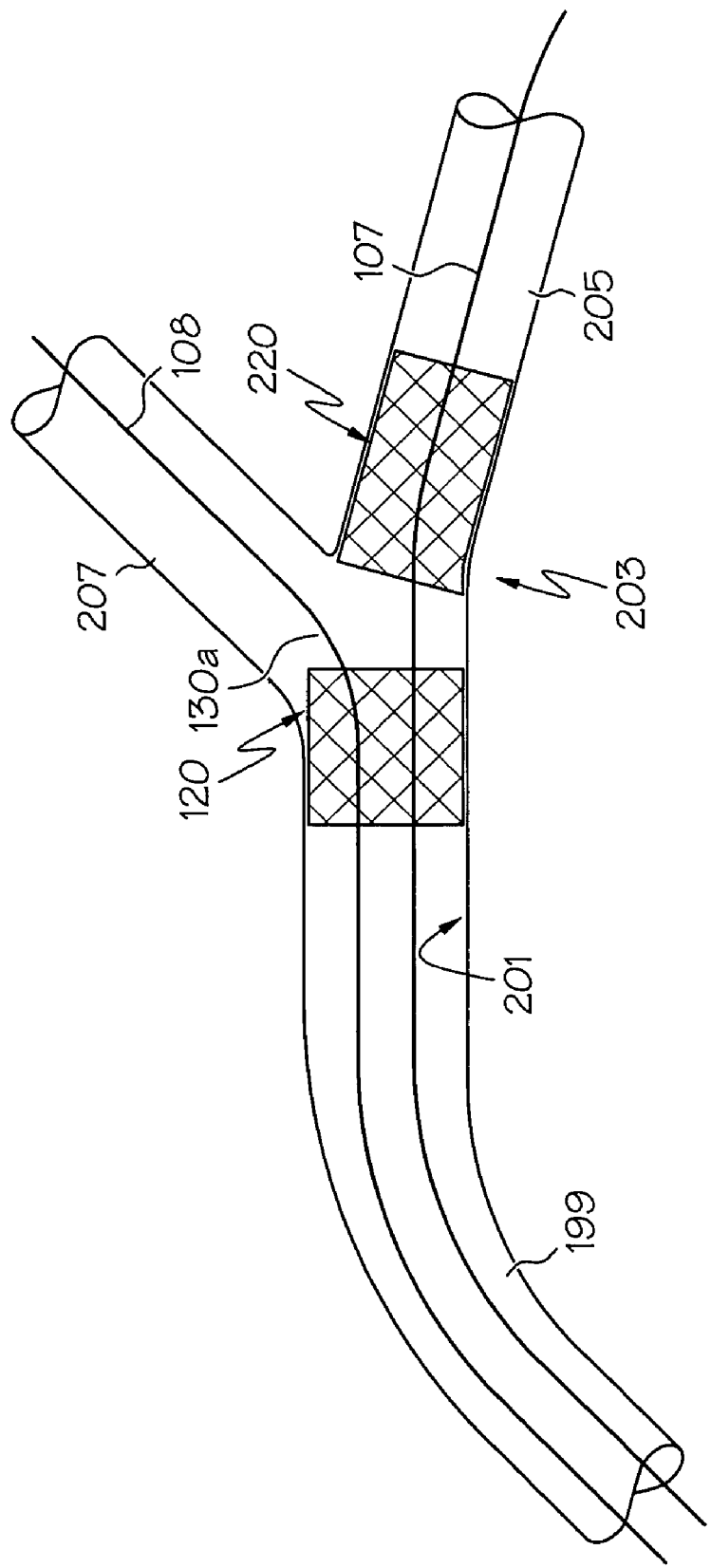
FIG. 12 is a side view of a vessel wherein the stents shown in FIG. 11 are depicted as being delivered therein.

As shown in FIG. 12, the extension of the secondary guidewire 108 between the stents 120 and 220 allows the stents to be rotatably aligned at the bifurcation 203 without the need to align a particular side or opening of a stent with the side branch 207 so that when the stents are deployed by expansion of the balloon or other delivery mechanism(s) access from the main vessel 199 to the secondary branch 207 is maintained between the adjacent deployed stents 120 and 220. In some embodiments, the stents 120 and 220 are substantially simultaneously deployed by expansion of the balloon so that at least a portion of the first stent 120 is positioned proximal of the secondary branch 207 and at least a portion of the second stent is substantially positioned distal of the secondary branch 207 within the first branch 205. Stents 120 and 220 may be positioned in any manner desired at the vessel bifurcation. For example the stents may be longitudinally adjacent one another, in contact with one another, in an overlapping or partially overlapping arrangement, etc.

Figure 13:
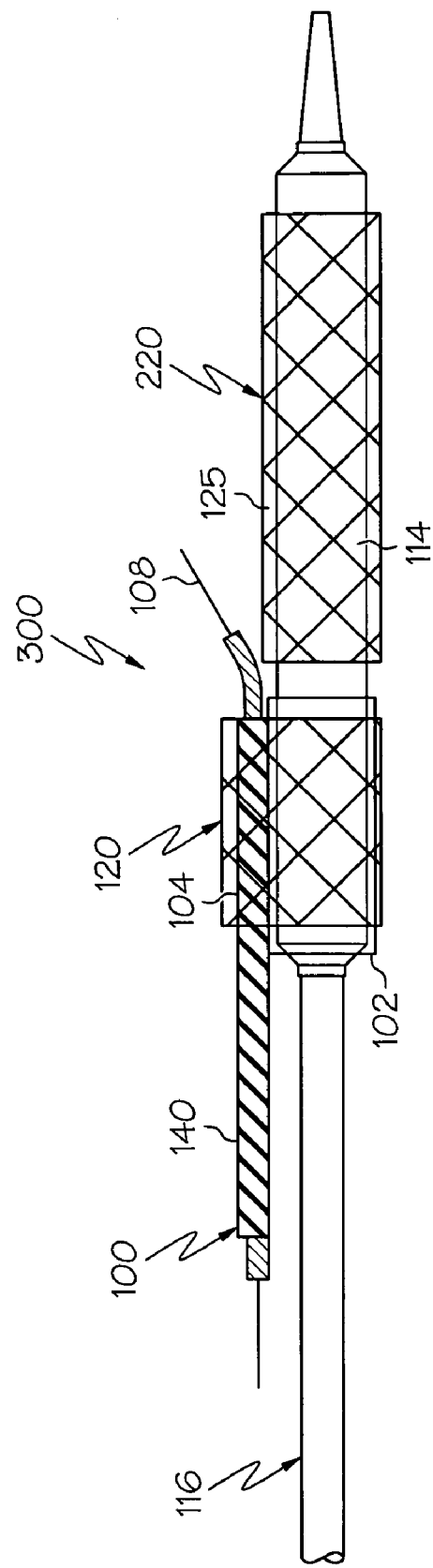
FIG. 13 is a cross-sectional side view of an embodiment of the invention wherein a catheter system includes a first stent mounted on a rotatable sheath and a second stent mounted longitudinally adjacent thereto.
Figure 14:
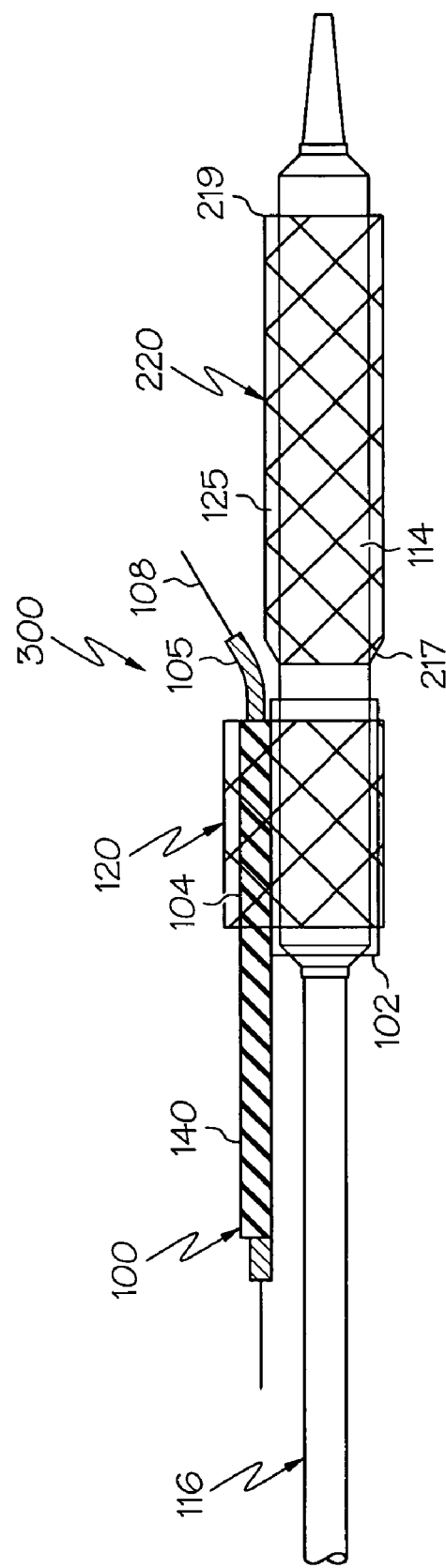
FIG. 14 is a cross-sectional side view of an embodiment of the invention wherein a catheter system includes a first stent mounted on a rotatable sheath and a second stent mounted longitudinally adjacent thereto.

In some embodiments, such as in the example shown in FIG. 13, only one of the stents 120 and 220 is disposed about the sheath 102. As such, one of the stents is effectively rotatable about the catheter 116 during advancement and the other remains fixedly disposed about the balloon 114. For example, in the embodiment shown in FIG. 13 the first stent 120 is disposed about the rotatable sheath 102 and secondary guidewire housing 104, while the second stent 220 is positioned longitudinally adjacent thereto and is fixedly engaged to the balloon 114 prior to delivery.

In some embodiments the second stent 220 includes a proximal end region 217 and/or a distal end region 219 which is tapered radially inward toward the balloon 114. The tapered end region may be provided to the second stent 220 by crimping the end region 217 to a narrower diameter than the rest of the stent 220 or by using a stent design which includes such a tapered configuration. By crimping one or both end regions down on to the balloon 114, the stent is provided with improved securement characteristics to reduce inadvertent longitudinal migration of the stent along the catheter 116. In addition, by providing the proximal end region 217 of the second stent 220 with a tapered configuration the distal end or tip 105 of the secondary guidewire housing 104 will be maintained in closer radial proximity to the catheter while having a greater degree of play. Furthermore, the tapered end region 217 of the second stent 220 allows the assembly 100 to more freely rotate as less of the stent is externally exposed, but in addition the assembly will also be able to rotate with minimal chance of interference from interaction between the secondary guidewire housing 104 and the second stent 220. In some embodiments stent 120 is also provided with one or more tapered end regions.

Figure 15:
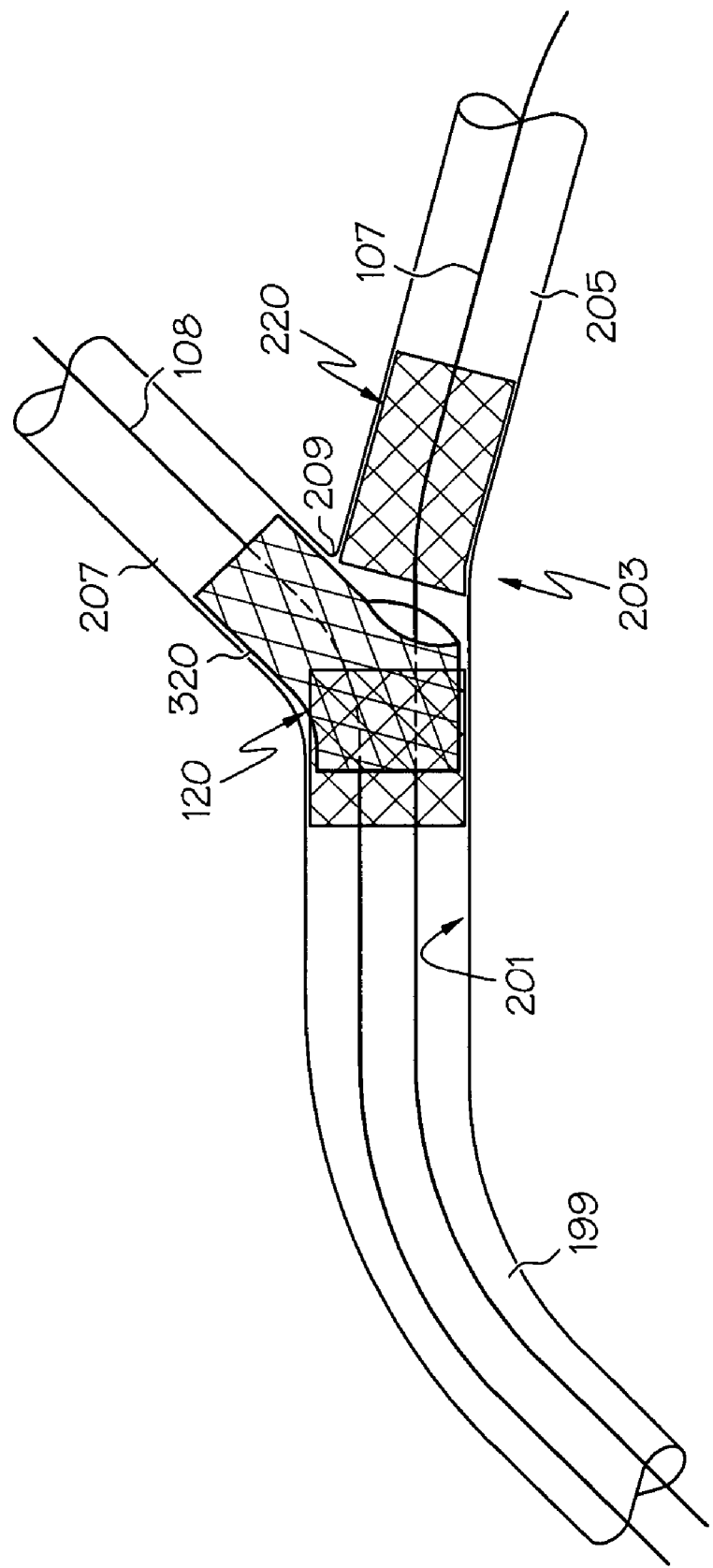
FIG. 15 is a side view of the vessel shown in FIG. 11 wherein a third stent has been subsequently delivered.
Figure 16:
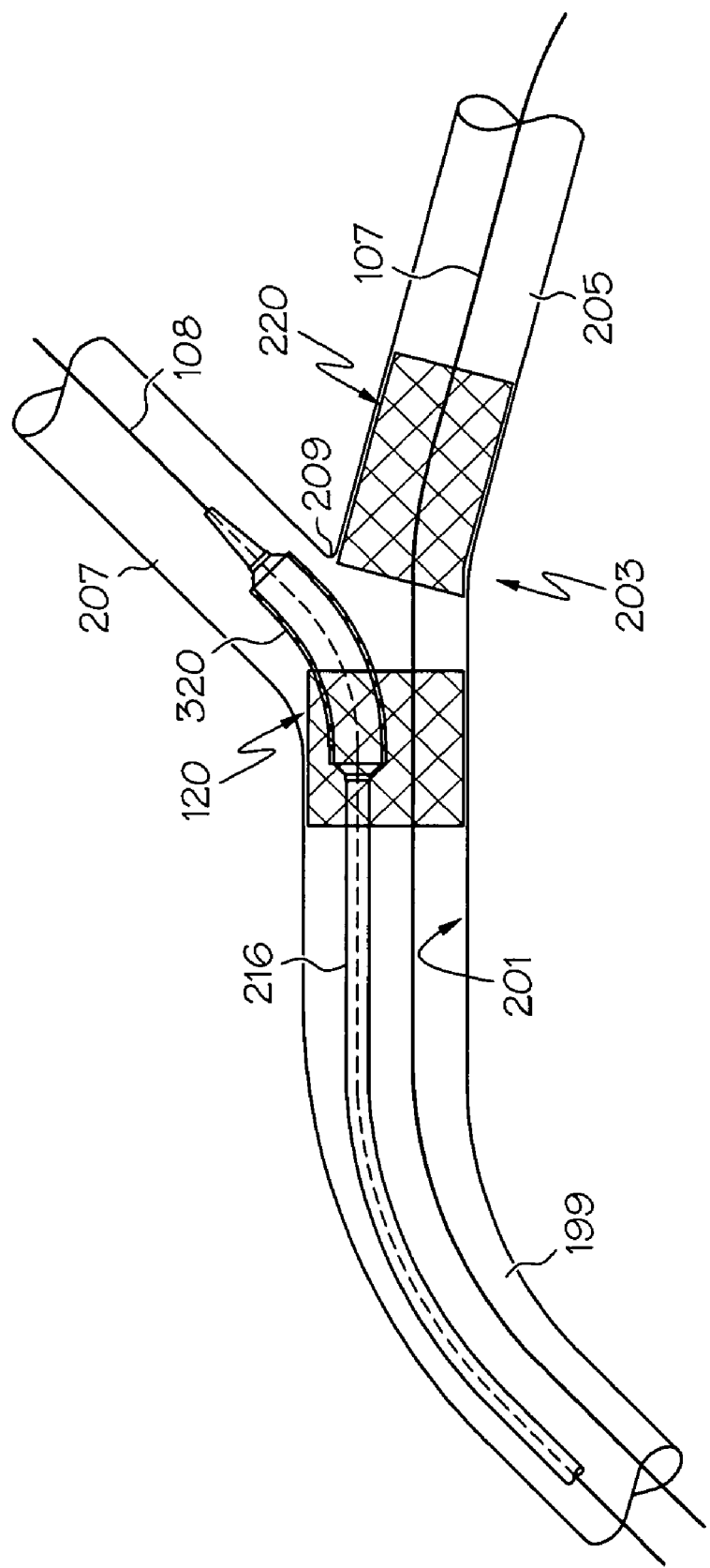
FIG. 16 is a side view of the vessel shown in FIG. 11 wherein a second catheter assembly is shown delivering a third stent.

In some embodiments, such as in the example shown in FIG. 15, it may be desirable or necessary to deploy a third stent 320 to the bifurcation 203 in order to provide additional coverage and/or support to the secondary branch 207 and/or the carina 209 of the bifurcation 203.

Where a third stent 320 is desired to be deployed a second catheter 216, such as is depicted in FIG. 16, may be advanced along the secondary guidewire 108 through the deployed stent 120 to deploy the third stent 320 in the second branch 207 and/or other locations. Likewise additional catheter assemblies may be advanced along either or both guidewires 107 and 108 to deploy additional stents at or around the bifurcation 203. Alternatively catheter 116 may have multiple stents 120, 220, 320, or more, positioned along various regions of the catheter shaft 144 and/or sheath 102 to provide a single catheter system capable of deploying any number of stents desired.

Figure 17:
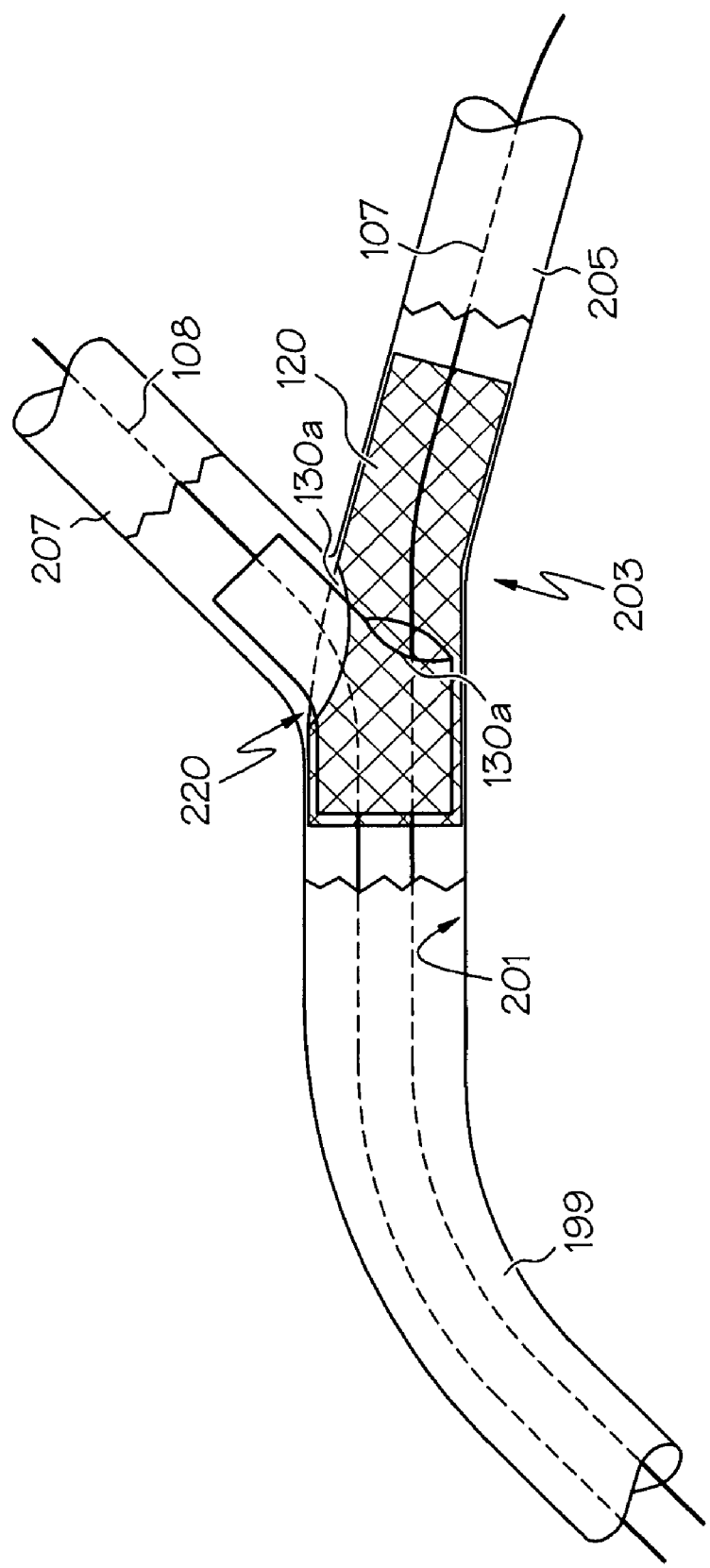
FIG. 17 is a side view of a vessel wherein two stents have been delivered by two catheter systems of type embodied in FIG. 5.

In some embodiments, such as in the example shown in FIG. 17 a vessel bifurcation 203 may be treated using two catheter systems 300 of the type shown in FIGS. 4 and 5 and described above, to deliver a pair of stents 120 and 220 to the bifurcation 203, so that when delivered, the stents 120 and 220 support the bifurcation 203 with a so-called 'culotte' configuration wherein overlapping portions of the stents are positioned in the trunk or main vessel 199 of the bifurcation 203 with a portion of one stent 120 extending into a first branch 205 and a portion of the other stent 220 extending into a second branch 207.

In order to properly position the stents 120 and 220 in the manner desired, the first stent 120 is delivered to the bifurcation in the manner described above and depicted in FIGS. 5 and 9. To reiterate, the catheter 116, is advanced along the secondary guidewire 108 and is also pushed through the vessel 199 or advanced along the primary guidewire 107. The rotatable assembly 100, described in detail above, allows the stent 120 to rotate into position at the bifurcation 203 to align the secondary opening 130a of the stent 120 with the secondary branch 207 of the vessel 199.

Figure 18:
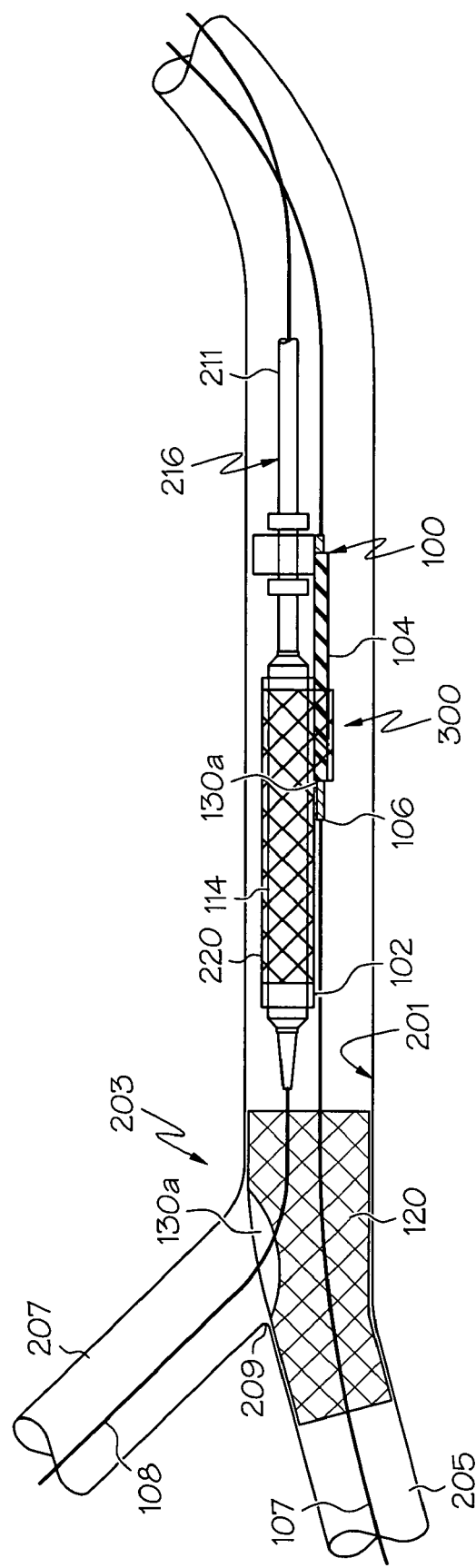
FIG. 18 is a side view of the vessel shown in FIG. 17 wherein the second catheter system is shown being advanced along the guidewires to orient the second stent for delivery at least partially through the previously deployed first stent.

Once the first stent 120 is delivered in this or some other manner a second catheter 216, such as is shown in FIG. 18 is advanced along the guidewires 107 and 108 with the opposite orientation than that of the first catheter 116 depicted in FIG. 5. In other words, the secondary guidewire housing 104 of the second catheter 216 is advanced along the primary guidewire 107 while the primary guidewire housing 211 is advanced along the secondary guidewire 108. As a result, when the second catheter 216 approaches the bifurcation 203 the stent 220 will be rotated such that the secondary opening 130a, of the secondary stent 220 is aligned with the first vessel branch 205. Once properly aligned, the stent 220 is deployed, in the manner shown in FIG. 16 so that a proximal portion of both stents overlap, proximal to the carina 209 and a distal portion of the first stent 120 extends into the first vessel branch 205 and a distal portion of the of the second stent 220 extends into the second vessel branch 207 through the secondary opening 130a of the first stent 120. The secondary opening 130a of the second stent 220 defines a flow path in fluid communication with the flow path defined by the distal portion of the first stent 120.

In some embodiments it may be desirable to delivery more than one stent which require orientation at one or more vessel bifurcations on a single catheter system. For example, in the embodiment shown in FIG. 19 a system 300 is shown wherein the catheter 116 includes a first rotatable sheath 102 having at least one first stent 120 disposed thereabout and at least one second rotatable sheath 202 with at least one second stent 220 disposed thereabout prior to delivery of the stents. To ensure that each stent 120 and 220 or more specifically each sheath 102 and 202 is independently rotatable, sheath 102 includes a secondary guidewire housing 104 which is advanced along secondary guidewire 108 in order to align the sheath 102 and thus the stent 120 so that the secondary opening 130a of the stent 120 is aligned with the secondary passage 207 in the manner such as described above. Likewise, sheath 202 is provided with a tertiary guidewire housing 204 which is advanced along a tertiary guidewire 109 so that the secondary opening 130a of the stent 220 is aligned with a third branch 213 within the vessel 199.

In some embodiments the tertiary guidewire 109 passes under the first stent 120 before the tertiary guidewire housing 204. In this arrangement the first stent 120 and assembly 100 is rotatable about the tertiary guidewire 109.

The catheter 116 may include separate balloons for delivery of the stents 120 and 220. For example in the embodiment shown in FIG. 19, prior to delivery of the stent 120 first sheath 102 is rotatable about a first balloon 114a and prior to delivery of stent 220 second sheath 202 is rotatable about a second balloon 114b.

Figure 19:
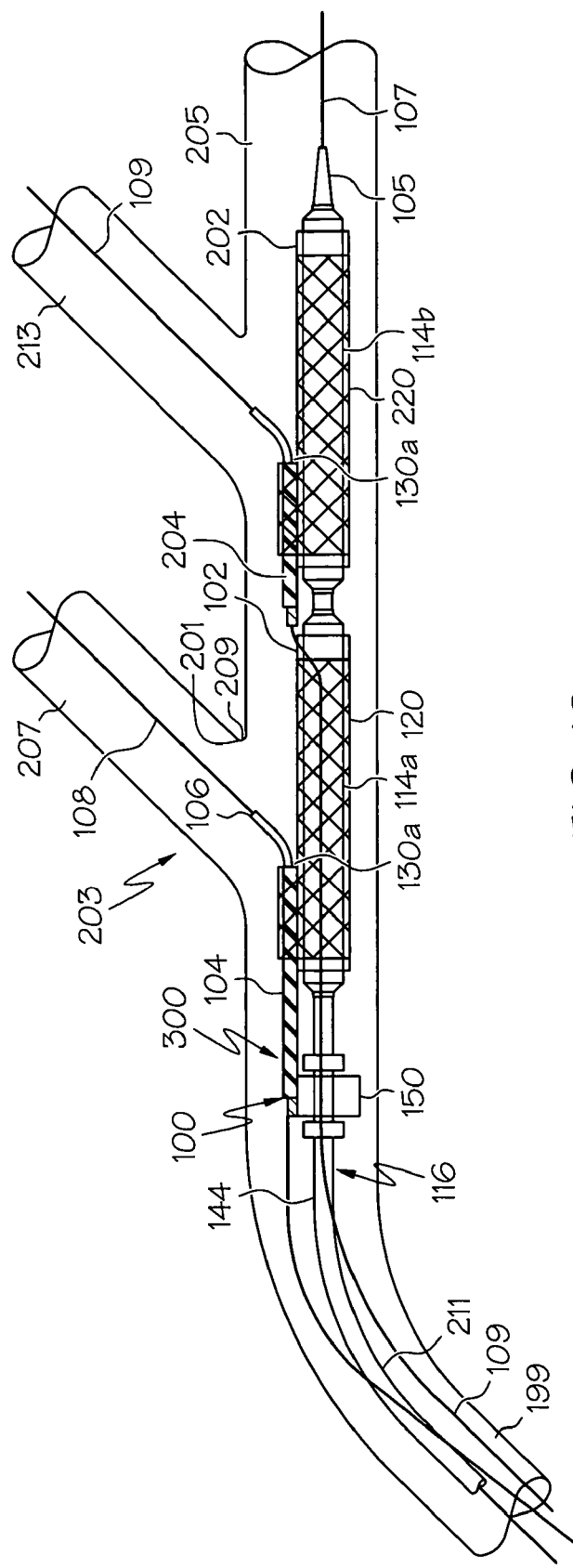
FIG. 19 is a side view of an embodiment of the invention shown within a vessel.
Figure 20:
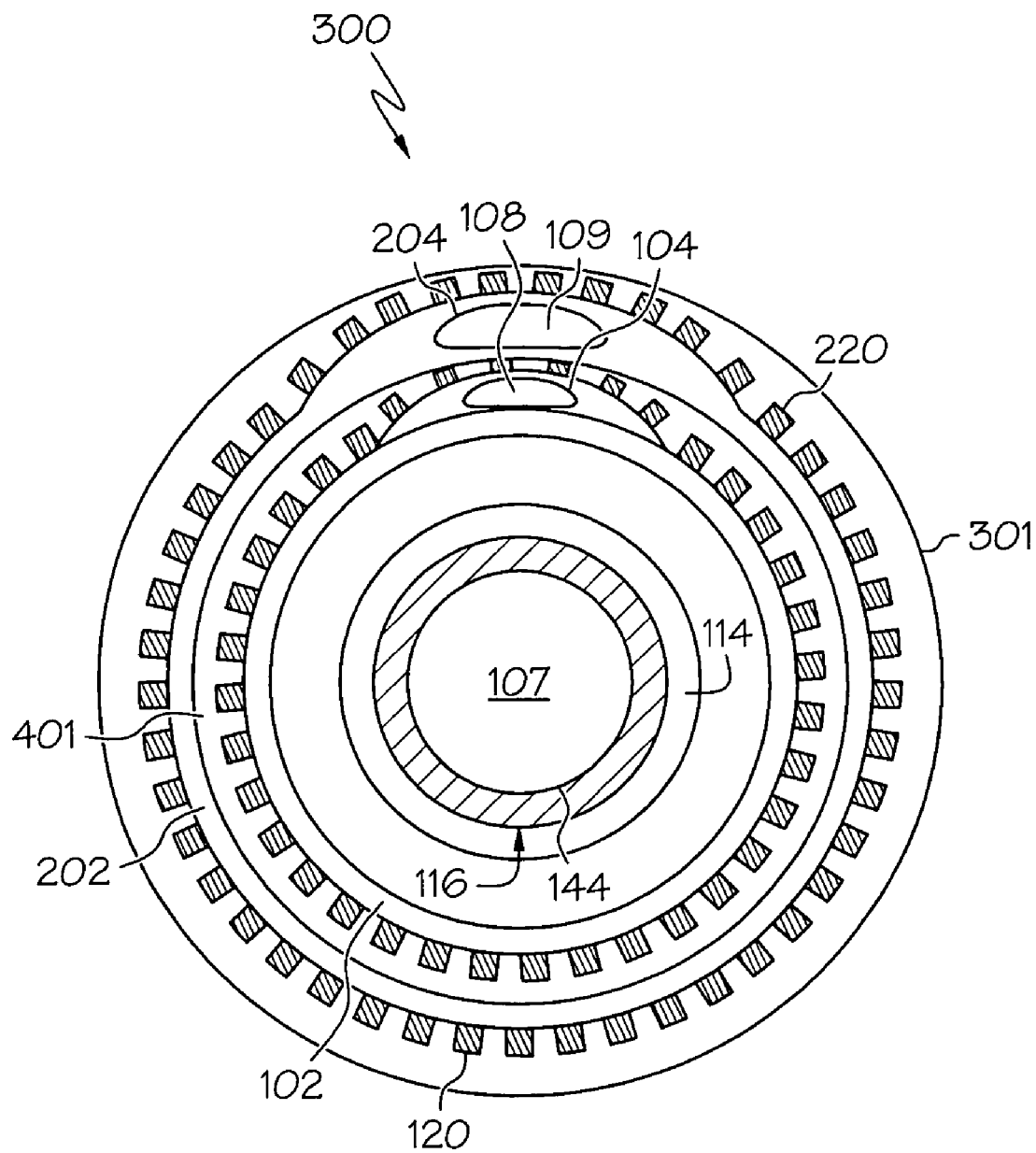
FIG. 20 is a cross-sectional view of an embodiment of the invention.

In the embodiment shown in FIG. 19 the separately rotatable sheathes 102 and 202 are longitudinally adjacent one another. The sheathes may be positioned anywhere desired on the catheter 116. In some embodiments however, multiple sheathes may be radially adjacent one another with one sheath and stent positioned about another independently rotatable sheath and stent. An example of such an embodiment is shown in FIG. 20, wherein a catheter is shown having a first sheath 102 disposed at least partially about the second stent 220 and/or second sheath 202. Second sheath 202 is rotatable about the catheter shaft 144 and/or balloon 114, and the first sheath 102 may be independently rotatable about the second stent 220. In this configuration the first stent 120 may be a self-expandable stent which is deployed before the second stent. The catheter 116 may include a retaining member or covering (sheath) 301 which retains the stent 120 in the unexpanded state. When the retaining member 301 is withdrawn the stent 120 is free to deploy off of the rotatable sheath 102.

In some embodiments rotatable sheath 102 may be constructed from a bio-absorbable material which when fully absorbed by the body allows the second stent 220 to be subsequently deployed by self-expansion or balloon expansion as the characteristics of the stent 220 and catheter 116 dictate. Alternatively, the sheath 102 may include a pull back member which following delivery of the first stent 120 as actuated to expose the second stent 220 for release or subsequent balloon expansion. In yet another alternative, sheath 102 may double as a graft member and may be deployed along with the second stent 220.

If desired, particularly in embodiments wherein the second rotatable sheath 202 is retracted or withdrawn from about the first stent 120 prior to delivery a lubricious coating 401 may be utilized to encourage retraction and/or minimize frictional interference between the sheath 202 and stent 120. In some embodiments the lubricious coating 401 may be applied between or on any of the various elements of the system 300.

The invention has been described with reference to the embodiments. Obviously, modifications and alterations will occur to others upon a reading and understanding of this specification. For example, many of the illustrated embodiments use a balloon to expand the stent although, as briefly noted above, a self expanding, self deploying or hybrid expandable stent can be used without departing from the features of the present invention. The invention is intended to include all such modifications and alterations thereof.

Furthermore, it is noted that the various embodiments shown and described U.S. patent application Ser. No. 10/375,689, filed Feb. 27, 2003 and U.S. patent application Ser. No. 10/657,472, filed Sep. 8, 2003 both of which are entitled Rotating Balloon Expandable Sheath Bifurcation Delivery; U.S. patent application Ser. No. 10/747,546, filed Dec. 29, 2003 and entitled Rotating Balloon Expandable Sheath Bifurcation Delivery System; and U.S. patent application Ser. No. 10/757,646, filed Jan. 13, 2004 and entitled Bifurcated Stent Delivery System may be incorporated and/or utilized with the various embodiments described herein.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

With this description, those skilled in the art may recognize other equivalents to the specific embodiment described herein. Such equivalents are intended to be encompassed by the claims attached hereto.

The invention claimed is:

1. A catheter assembly comprising:
   a catheter, the catheter comprising a catheter shaft;
   a first rotatable sheath, the first rotatable sheath including a radial outer surface and a radial inner surface, the first rotatable sheath being disposed about and rotatable relative to a portion of the catheter shaft, the first rotatable sheath having a length substantially less than that of the catheter shaft, the first rotatable sheath being expandable from a reduced sheath state to an expanded sheath state, in the reduced sheath state the first sheath being rotatable about the portion of the catheter shaft;
   a first guidewire housing, the first guidewire housing defining a first guidewire lumen for passage of a first guidewire therethrough, at least a portion of the first guidewire housing being engaged to the radial outer surface of the first rotatable sheath;
   a first stent, the first stent being expandable from a reduced stent state to an expanded stent state, in the reduced stent state the stent being disposed about at least a portion of the first rotatable sheath and at least a portion of the first guidewire housing; and
   a second stent, the second stent being expandable from a reduced stent state to an expanded stent state, in the reduced stent state the second stent being disposed about the catheter shaft adjacent to the first stent.

2. The catheter assembly of claim 1 wherein the portion of the catheter shaft comprises a balloon.

3. The catheter assembly of claim 2 wherein when the second stent is in the reduced stent state the second stent is disposed about the catheter shaft longitudinally adjacent to the first rotatable sheath.

4. The catheter assembly of claim 2 wherein when the second stent is in the reduced stent state the second stent is positioned longitudinally adjacent to the first stent along the first rotatable sheath.

5. The catheter assembly of claim 1 wherein when the second stent is in the reduced stent state the second stent is disposed about the catheter shaft longitudinally adjacent to the first rotatable sheath.

6. The catheter assembly of claim 1 wherein when the second stent is in the reduced stent state the second stent is positioned longitudinally adjacent to the first stent along the first rotatable sheath.

7. The catheter assembly of claim 1 wherein when the first stent is in the reduced stent state at least a portion of the first stent overlays at least a portion of the first guidewire housing.

8. The catheter assembly of claim 7 wherein when the first stent is in the reduced stent state at least a distal portion of the first guidewire housing extends externally from the fist stent to a position between the first stent and the second stent.

9. The catheter assembly of claim 8 wherein the second stent comprises a distal end region, a proximal end region and a body region therebetween, in the reduced stent state at least the proximal end region having a diameter less than that of the body region.

10. The catheter assembly of claim 8 wherein the diameter of at least the proximal end region tapers from the body region.

11. The catheter assembly of claim 1 further comprising a second rotatable sheath, the second rotatable sheath being disposed about a portion of the catheter shaft longitudinally adjacent the first rotatable sheath, the second rotatable sheath being expandable from a reduced sheath state to an expanded sheath state, in the reduced sheath state the second sheath being rotatable about the portion of the catheter shaft longitudinally adjacent the first rotatable sheath, the second rotatable sheath having a length substantially less than that of the catheter shaft; and
   a second guidewire housing, the second guidewire housing defining a second guidewire lumen for passage of a second guidewire therethrough, at least a portion of the second guidewire housing being engaged to the second rotatable sheath.

12. The catheter assembly of claim 11 wherein the portion of the catheter shaft comprises a first balloon and the portion of the catheter longitudinally adjacent the first rotatable sheath comprises a second balloon.

13. The catheter assembly of claim 1 further comprising a second rotatable sheath, when the first stent is in the reduced stent state the second rotatable sheath is rotatably disposed about at least a portion of the first stent, in the reduced stent state the second stent is disposed about the second rotatable sheath.

14. The catheter assembly of claim 13 wherein the second rotatable sheath is bio-absorbable.

15. The catheter assembly of claim 13 wherein the second rotatable sheath is retractable from about the first stent.

16. The catheter assembly of claim 13 wherein the second rotatable sheath is expandable from a reduced sheath state to an expanded sheath state.

17. The catheter assembly of claim 13 wherein at least a portion of at least one member of the group consisting of the first stent, the second stent, the first rotatable sheath, the second rotatable sheath, and any combination thereof is coated with at least one therapeutic agent.

18. The catheter assembly of claim 1 wherein the first stent is selected from at least one member of the group consisting of: a self-expanding stent, a balloon-expandable stent, a hybrid expandable stent and any combination thereof.

19. The catheter assembly of claim 1 wherein the second stent is selected from at least one member of the group consisting of: a self-expanding stent, a balloon-expandable stent, a hybrid expandable stent and any combination thereof.

20. The catheter assembly of claim 1 wherein at least a portion of at least one member of the group consisting of the first stent, the second stent, the first rotatable sheath and any combination thereof is coated with at least one therapeutic agent.

21. The catheter assembly of claim 20 wherein the at least one therapeutic agent is at least one non-genetic therapeutic agent selected from at least one member of the group consisting of anti-thrombogenic agents such as heparin, heparin derivatives, urokinase, and PPack (dextrophenylalanine proline arginine chloromethylketone); anti-proliferative agents such as enoxaprin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/anti-proliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine and ropivacaine; anti-coagulants such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factor inhibitors, growth factor receptor antagonists, transcriptional activators, and translational promoters, vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin; bifunctional molecules consisting of an antibody and a cytotoxin; cholesterol-lowering agents; vasodilating agents; and agents which interfere with endogenous vascoactive mechanisms, and any combinations thereof.

22. The catheter assembly of claim 20 wherein the at least one therapeutic agent is at least one genetic therapeutic agent selected from at least one member of the group consisting of: anti-sense DNA and RNA; DNA coding for anti-sense RNA, tRNA or rRNA to replace defective or deficient endogenous molecules; angiogenic factors including growth factors such as acidic and basic fibroblast growth factors, vascular endothelial growth factor, epidermal growth factor, transforming growth factor .alpha. and .beta., platelet-derived endothelial growth factor, platelet-derived growth factor, tumor necrosis factor .alpha., hepatocyte growth factor and insulin like growth factor; cell cycle inhibitors including CD inhibitors, thymidine kinase ("TK") and other agents useful for interfering with cell proliferation; at least one of the family of bone morphogenic proteins ("BMP's") such as BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Any of BMP-2, BMP-3, BMP-4, BMP-5, BMP-6 and BMP-7; dimeric proteins such as homodimers, heterodimers, or combinations thereof, alone or together with other molecules; molecules capable of inducing an upstream or downstream effect of a BMP such as "hedgehog" proteins, or the DNA's encoding them and any combinations thereof.

23. The catheter assembly of claim 20 wherein the at least one therapeutic agent is at least one type of cellular material selected from at least one member of the group consisting of: cells of human origin (autologous or allogeneic); cells of non-human origin (xenogeneic) and any combination thereof.

24. The catheter assembly of claim 23 wherein the cellular material is selected from at least one member of the group consisting of: side population cells; lineage negative cells; lineage negative CD34$^-$ cells; lineage negative CD34$^+$ cells; lineage negative$^-$ cKit$^+$ cells; mesenchymal stem cells; cord blood bells; cardiac or other tissue derived stem cells; whole bone marrow; bone marrow mononuclear cells; endothelial progenitor cells; satellite cells; muscle derived cells; go cells; endothelial cells; adult cardiomyocytes; fibroblasts; smooth muscle cells; cultures of mesenchymal stem cells with 5-aza forces differentiation into cardiomyocytes; adult cardiac fibroblasts+5-aza; genetically modified cells; tissue engineered grafts; MyoD scar fibroblasts; Pacing cells; embryonic stem cell clones; embryonic stem cells; fetal or neonatal cells; immunologically masked cells; tissue engineered grafts; genetically modified cells; teratoma derived cells and any combinations thereof.

25. The catheter assembly of claim 20 wherein the at least one therapeutic agent comprises at least one polymer coating, the at least one coating selected from at least one member of the group consisting of: polycarboxylic acids; cellulosic polymers, including cellulose acetate and cellulose nitrate; gelatin; polyvinylpyrrolidone; cross-linked polyvinylpyrrolidone; polyanhydrides including maleic anhydride polymers; polyamides; polyvinyl alcohols; copolymers of vinyl monomers such as EVA; polyvinyl ethers; polyvinyl aromatics; polyethylene oxides; glycosaminoglycans; polysaccharides; polyesters including polyethylene terephthalate; polyacrylamides; polyethers; polyether sulfone; polycarbonate; polyalkylenes including polypropylene, polyethylene and high molecular weight polyethylene; halogenated polyalkylenes including polytetrafluoroethylene; polyurethanes; polyorthoesters; proteins; polypeptides; silicones; siloxane polymers; polylactic acid; polyglycolic acid; polycaprolactone; polyhydroxybutyrate valerate and blends and copolymers thereof; coatings from polymer dispersions such as polyurethane dispersions (BAYHDROL®, etc.), fibrin, collagen and derivatives thereof; polysaccharides such as celluloses, starches, dextrans, alginates and derivatives; hyaluronic acid; squalene emulsions; polyacrylic acid, a copolymer of polylactic acid and polycaprolactone; medical-grade biodegradable materials such as PGA-TMC, Tyrosine-Derived Polycarbonates and arylates; polycaprolactone co butyl acrylate and other co polymers; Poly-L-lactic acid blends with DL-Lactic Acid; Poly(lactic acid-co-glycolic acid); polycaprolactone co PLA; polycaprolactone co butyl acrylate and other copolymers; Tyrosine-Derived Polycarbonates and arylate; poly amino acid; polyphosphazenes; polyiminocarbonates; polydimethyltrimethylcarbonates; biodegradable CA/PO$_4$'s; cyanoacrylate; 50/50 DLPLG; polydioxanone; polypropylene fumarate; polydepsipeptides; macromolecules such as chitosan and Hydroxylpropylmethylcellulose; surface erodible material; maleic anhydride copolymers; zinc-calcium phosphate; amorphous polyanhydrides; sugar; carbohydrate; gelatin; biodegradable polymers; and polymers dissolvable in bodily fluids; A block copolymers; B block copolymers and any combinations thereof.

26. The catheter assembly of claim 1 further comprising a lubricious coating, the lubricious coating positioned between at least a portion of the first rotatable sheath and the a portion of the catheter shaft.

27. The catheter assembly of claim 1 wherein the first rotatable sheath is at least partially constructed from a hydrophilic polymer material.

28. The catheter assembly of claim 1 wherein the first rotatable sheath is at least partially constructed from a tecophilic material.

29. The catheter assembly of claim 1 wherein the first rotatable sheath is at least partially constructed from a first material and a second material.

30. The catheter assembly of claim 29 wherein the first material is a polymer matrix and the second material is at least one distinct member of reinforcing material at least partially supported within the polymer matrix.

31. The catheter assembly of claim 30 wherein polymer matrix is selected from at least one material from the group consisting of: hydrophilic polyurethanes, aromatic polyurethanes, polycarbonate base aliphatic polyurethanes, engineering polyurethane, elastomeric polyamides, block polyamide/ethers, polyether block amide, silicones, polyetherester, polyester, polyester elastomer, polyethylene and any combination thereof.

32. The catheter assembly of claim 30 wherein the reinforcing material is selected from at least one material of the group consisting of polyamide, polyethylene, high-density polyethylene, polyetheretherketone, polyimide, polyetherimide, liquid crystal polymers, acetal, and any combination thereof.

33. The catheter assembly of claim 1 wherein the first rotatable sheath is at least partially constructed from at least one material of the group consisting of: hydrophilic polyurethanes, aromatic polyurethanes, polycarbonate base aliphatic polyurethanes, engineering polyurethane, elastomeric polyamides, block polyamide/ethers, polyether block amide, silicones, polyether-ester, polyester, polyester elastomer, polyethylene, polyimide, high-density polyethylene, polyetheretherketone, polyimide, polyetherimide, liquid crystal polymers, acetal, and any combination thereof.

* * * * *

UNITED STATES PATENT AND TRADEMARK OFFICE
CERTIFICATE OF CORRECTION

Page 1 of 1

PATENT NO. : 8,012,192 B2
APPLICATION NO. : 10/780937
DATED : September 6, 2011
INVENTOR(S) : Tracee Eidenschink, Jan Weber and Daniel Gregorich It is certified that error appears in the above-identified patent and that said Letters Patent is hereby corrected as shown below:

Column 20
Line 63: delete "polyimide" and insert therefor --polyamide--

Signed and Sealed this
Eighteenth Day of October, 2011

David J. Kappos
*Director of the United States Patent and Trademark Office*